US008702628B2

(12) United States Patent
Horii

(10) Patent No.: US 8,702,628 B2
(45) Date of Patent: Apr. 22, 2014

(54) PHYSIOLOGICAL SOUND EXAMINATION DEVICE

(75) Inventor: Noriaki Horii, Kyoto (JP)

(73) Assignee: Panasonic Corporation, Osaka (JP)

( * ) Notice: Subject to any disclaimer, the term of this patent is extended or adjusted under 35 U.S.C. 154(b) by 242 days.

(21) Appl. No.: 13/319,861

(22) PCT Filed: Mar. 10, 2011

(86) PCT No.: PCT/JP2011/001408
§ 371 (c)(1),
(2), (4) Date: Nov. 10, 2011

(87) PCT Pub. No.: WO2011/114669
PCT Pub. Date: Sep. 22, 2011

(65) Prior Publication Data
US 2012/0059280 A1  Mar. 8, 2012

(30) Foreign Application Priority Data
Mar. 18, 2010  (JP) .................................. 2010-062324

(51) Int. Cl.
*A61B 7/00* (2006.01)
(52) U.S. Cl.
USPC ......................................................... 600/586
(58) Field of Classification Search
USPC ............................................ 600/561; 381/67
See application file for complete search history.

(56) References Cited

U.S. PATENT DOCUMENTS

| 6,443,907 B1 | 9/2002 | Mansy et al. |
| 2003/0018276 A1 | 1/2003 | Mansy et al. |
| 2005/0033144 A1 | 2/2005 | Wada |
| 2010/0145210 A1 | 6/2010 | Graff et al. |
| 2010/0160807 A1 | 6/2010 | Schmidt et al. |

FOREIGN PATENT DOCUMENTS

| JP | 2004-512066 | 4/2004 |
| JP | 3604127 | 12/2004 |
| JP | 2005-27751 | 2/2005 |
| JP | 2007-236534 | 9/2007 |
| JP | 2009-240527 | 10/2009 |
| JP | 2009-540971 | 11/2009 |
| WO | 02/30280 | 4/2002 |
| WO | 2004/002317 | 1/2004 |
| WO | 2008/000254 | 1/2008 |
| WO | 2008/000259 | 1/2008 |

OTHER PUBLICATIONS

International Search Report issued Jun. 21, 2011 in International (PCT) Application No. PCT/JP2011/001408.

*Primary Examiner* — Brian Szmal
(74) *Attorney, Agent, or Firm* — Wenderoth, Lind & Ponack, L.L.P.

(57) ABSTRACT

A physiological sound examination device includes a physiological sound measurement unit; a power calculation unit which calculates power of a first physiological sound and power of a second physiological sound, the first physiological sound being one of two different kinds of physiological sounds measured by the physiological sound measurement unit in a same time period and the second physiological sound being the other of the two different kinds of physiological sounds; a power comparison unit which compares first power indicating the power of the first physiological sound and second power indicating the power of the second physiological sound, to calculate a comparison result indicating a ratio or a difference between the first power and the second power; and a determination unit which determines whether or not a measurement position of the physiological sound is appropriate, by comparing the comparison result with a threshold.

22 Claims, 26 Drawing Sheets

| Measurement positions below the right clavicle | 1 (50mm outward) | 2 (25mm outward) | 3 (Appropriate position) | 4 (25mm inward) | 5 (50mm inward) |
|---|---|---|---|---|---|
| Power ratio (dB) | -24.5 | -19.2 | -16.5 | -14.2 | -10.7 |

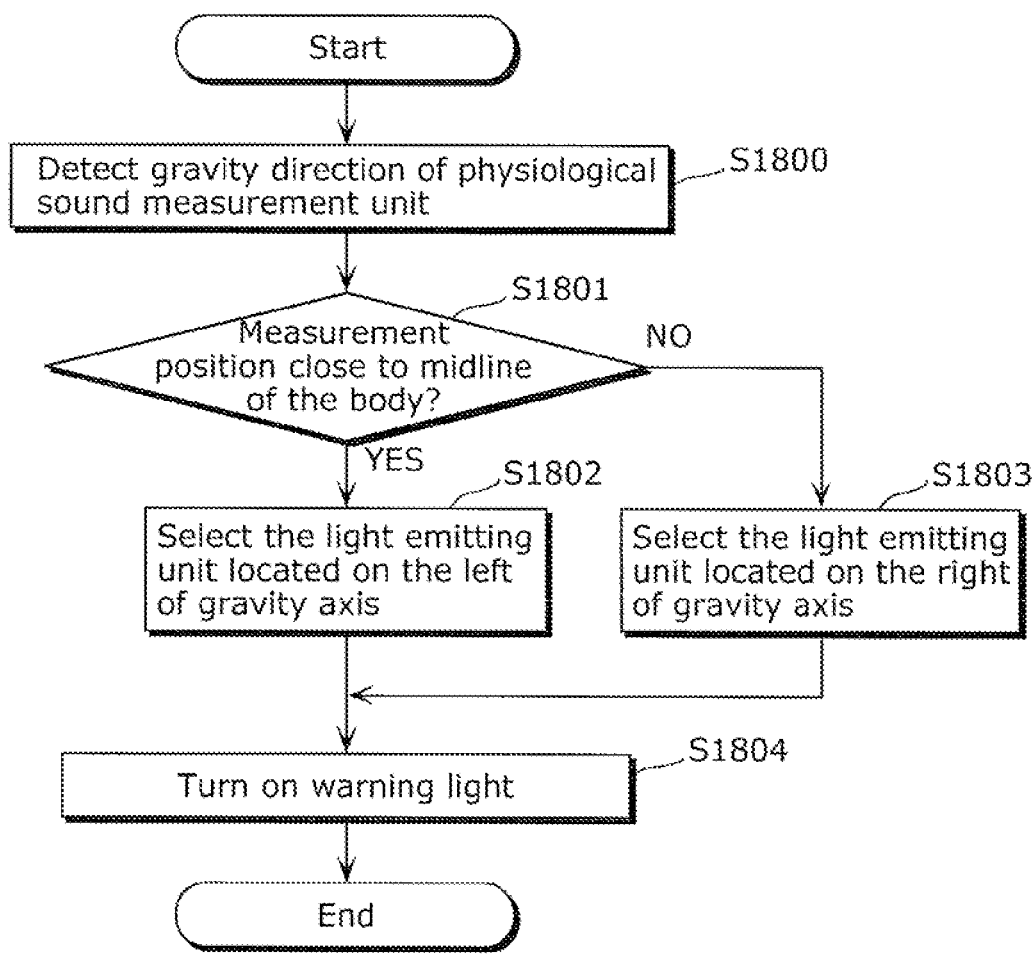

PHYSIOLOGICAL SOUND EXAMINATION DEVICE

BACKGROUND OF INVENTION

1. Technical Field

The present invention relates to a physiological sound examination device which estimates a state of a living body by obtaining a physiological sound of the living body and performing signal processing on the obtained physiological sound.

2. Background Art

In a hospital or the like, a doctor listens to a physiological sound of a patient, such as heart sound or lung sound, using a stethoscope to make a diagnosis. The diagnosis by auscultation is based on a subjective evaluation of the doctor. On this account, skill is required to make a correct diagnosis.

The lung sound refers to all sounds, except for sounds coming from the cardiovascular system, generated by the motion of breathing in the lungs and thorax regardless of whether normal or abnormal. Moreover, the lung sound is divided into a breath sound and an adventitious sound. The breath sound refers to a physiological sound whose source is airflow occurring in the respiratory tract by breathing. The adventitious sound refers to an abnormal sound, such as wheezing or pleural friction rub, caused in a pathological state. The sound source of breathing is thought to be in the respiratory tract which is relatively large.

Pneumothorax is one of lung diseases. Pneumothorax is an air space formed between the lung and the chest wall, and appears as a decrease in breath sound intensity in physical presentation. A method of detecting a state of pneumothorax has been disclosed (see PTL 1). More specifically, in this method, a sound wave is emitted from a speaker into the mouth and the trachea so that the emitted sound wave propagates through the body of the patient, and then the propagated sound wave is measured on the chest wall for signal processing.

With this method, a transfer function is calculated from the sound wave to be emitted and the sound wave measured on the chest wall, and an energy ratio between a low frequency band and a high frequency band is calculated using the transfer function. In this way, the state of pneumothorax is detected.

Moreover, as a method without emitting a sound wave from a speaker, PTL 1 also discloses a method of analyzing the lung sound measured on the chest wall. In this method, frequency conversion is performed using a lung sound signal detected on the chest wall, and an energy ratio between a low frequency band and a high frequency band is calculated. In this way, a respiratory state is detected.

Here, for making a respiratory diagnosis, the doctor listens to the lung sound by placing a stethoscope on different positions of the body. A device which includes, in order to detect a measurement position of the lung sound, an acceleration sensor in a sensor for measuring the lung sound has been disclosed (see PTL 2).

With this device, output values of the acceleration sensor are integrated to calculate a moving distance of the sensor, so that the measurement position of the lung sound is automatically detected.

Furthermore, when a patient is in a remote area, a person other than the doctor places a microphone on a predetermined position of the body of the patient to measure the physiological sound and then transmits the measured physiological sound via a wired or wireless communication to the doctor who thus listens to the physiological sound to make a diagnosis.

In order for the doctor to be able to make a diagnosis even when the microphone is not placed on the predetermined position of the body of the patient, a device whereby more than one microphone is placed on the body of the patient to help the doctor make the diagnosis has been disclosed (see PTL 3).

With this device, a weighted sum is calculated using acoustic signals received from the microphones, so as to simulate an acoustic signal corresponding to a position where no microphone is placed. In this way, a diagnosis made in a remote area is supported.

CITATION LIST

Patent Literature

[PTL 1]
Japanese Unexamined Patent Application Publication No. 2004-512066
[PTL 2]
Japanese Unexamined Patent Application Publication No. 2005-27751
[PTL 3]
Japanese Patent Publication No. 3604127

SUMMARY OF INVENTION

In the case of a conventional technique for analyzing a physiological sound via the signal processing, a sensor for detecting the physiological sound needs to be placed on an appropriate position of the body. Thus, there is a problem that it is difficult for a person who is unfamiliar with auscultation to find the appropriate auscultation position (the measurement position of the physiological sound).

In particular, as the auscultation position of the lung sound or heart sound, bones such as clavicles and ribs need to be avoided to perform auscultation on the chest wall. Moreover, even when the sensor is placed on the chest wall, it is difficult to find how far the appropriate auscultation position is away from the midline of the body.

For example, when an auscultation position on the midclavicular line is to be found, it is difficult to determine the position of the midclavicular line. As in the case of PTL 1, when the decrease in breath sound intensity in physical presentation is detected via the signal processing, the auscultation position is extremely important.

Here, suppose that the method disclosed in PTL 2 is employed to determine whether or not the measurement position of the physiological sound is appropriate. In this case, even when a distance by which the sensor has moved from a predetermined position is calculated, the method of PTL 2 cannot determine whether or not the position of the sensor after the movement is appropriate for a measurement subject.

Moreover, suppose that the method disclosed in PTL 3 is employed. In this case, it should be noted that since the body includes organs, bones, muscles, and fat, various reflections or interference may occur while the physiological sound propagates through the body. On account of this, with the acoustic sound simulated based on the weighted sum calculated using the signals received from the microphones, it is difficult to accurately analyze the physiological sound.

The present invention is conceived in view of the aforementioned problem and has an object to provide a physiological sound examination device capable of accurately determining whether or not a measurement position of a physiological sound is appropriate.

In order to achieve the aforementioned object, a physiological sound examination device according to an aspect of the present invention includes: a physiological sound measurement unit which measures a physiological sound originating from vibration propagating through inside a living body of a measurement subject; a power calculation unit which calculates power of a first physiological sound and power of a second physiological sound, the first physiological sound being one of two different kinds of physiological sounds measured by the physiological sound measurement unit in a same time period and the second physiological sound being the other of the two different kinds of physiological sounds; a power comparison unit which compares first power indicating the power of the first physiological sound and second power indicating the power of the second physiological sound, to calculate a comparison result indicating a ratio or a difference between the first power and the second power both calculated by the power calculation unit; and a determination unit which determines whether or not a measurement position of the physiological sound measured by the physiological sound measurement unit is appropriate, by comparing the comparison result calculated by the power comparison unit with a threshold.

With this configuration, based on the power ratio or power difference between the two kinds of physiological sounds, whether the measurement position of the physiological sound is appropriate or not is determined. To be more specific, by using the difference in physical quantity between the measured two kinds of physiological sounds, it is accurately determined whether or not the measurement position of at least one of the two kinds of physiological sounds is appropriate.

Moreover, in the physiological sound examination device according to an aspect of the present invention, the physiological sound measurement unit may include: a first measurement unit which measures the physiological sound as the first physiological sound at a first site of the living body; and a second measurement unit which measures the physiological sound as the second physiological sound at a second site of the living body which is different from the first site, the power comparison unit may calculate the comparison result indicating a power ratio in a predetermined frequency band between the first power and the second power, and the determination unit may determine that a measurement position of the second physiological sound is inappropriate when (a) a difference value obtained by subtracting a predetermined reference power ratio from the power ratio is equal to or larger than a first threshold used as the threshold or (b) the difference value is equal to or smaller than a second threshold smaller than the first threshold.

With this configuration, when the power ratio between the physiological sounds measured at the two positions is significantly larger or smaller than the reference power ratio, it is determined that the measurement position of the second physiological sound is inappropriate.

In other words, based on the power ratio between the physiological sounds measured at the two positions, it is accurately determined whether or not the measurement position of one of the physiological sounds is appropriate.

Furthermore, in the physiological sound examination device according to an aspect of the present invention, the first measurement unit may measure the physiological sound as the first physiological sound at a position, as the first site, where a sternal notch is located, and the second measurement unit may measure the physiological sound as the second physiological sound at a position, as the second site, on a chest wall.

With this configuration, the physiological sound examination device can determine, with a higher degree of accuracy, whether or not the measurement position of the physiological sound is in a range which is appropriate for measuring the lung sound on the chest wall.

Moreover, the physiological sound examination device according to an aspect of the present invention may further include a display unit which displays an instruction, to the measurement subject or a measurer, to change the measurement position of the second physiological sound, when the determination unit determines that the measurement position of the second physiological sound is inappropriate, wherein the display unit may display the instruction to move the measurement position to a position farther away from a midline of the living body, when a result of the determination made by the determination unit indicates that the difference value is equal to or larger than the first threshold, and display the instruction to move the measurement position to a position closer to the midline of the living body, when the result of the determination indicates that the difference value is equal to or smaller than the second threshold.

With this configuration, when the measurement position is inappropriate, the physiological sound examination device can reliably show a direction to which the measurement position is to be changed to the measurer, for example. Thus, effective measurement support can be achieved.

Furthermore, in the physiological sound examination device according to an aspect of the present invention, the display unit may include at least one light emitting unit, and the at least one light emitting unit may display the instruction by emitting light, when the determination unit determines that the measurement position of the second physiological sound is inappropriate.

With this configuration, when the measurement position is inappropriate, the measurer can visually understand the direction to which the measurement position is to be changed, for example. More specifically, the physiological sound examination device allows the measurer to easily understand the instruction for the directional change.

Moreover, the physiological sound examination device according to an aspect of the present invention may further include a direction detection unit which detects a predetermined direction, wherein the direction detection unit may detect, as the predetermined direction, a direction from an upper half of the living body to a lower half of the living body, when the determination unit determines that the measurement position of the second physiological sound is inappropriate, and the display unit may: include a plurality of light emitting units including the at least one light emitting unit; cause a first light emitting unit, among the light emitting units, to emit light, when the result of the determination made by the determination unit indicates that the difference value is equal to or larger than the first threshold, the first light emitting unit being located on a right side or a left side of an axis which passes through the second measurement unit and is parallel to the detected predetermined direction; and cause a second light emitting unit, among the light emitting units, to emit light, when the result of the determination indicates that the difference value is equal to or smaller than the second threshold, the second light emitting unit being located on an opposite side of the axis with respect to the first light emitting unit.

With this configuration, when the measurement position is inappropriate, the measurer can visually understand whether to change the measurement position to the right or to the left. More specifically, the physiological sound examination device allows the measurer to easily understand the direction to which the measurement position is to be changed.

Furthermore, in the physiological sound examination device according to an aspect of the present invention, the determination unit may perform correction using: a first physical characteristic value indicating a physical characteristic value of the measurement subject of when the reference power ratio is set; a second physical characteristic value indicating a physical characteristic value of the measurement subject of when the first physiological sound and the second physiological sound are measured; and a preset correction formula.

With this configuration, the reference power ratio is corrected appropriately according to a change in physical characteristic of the measurement subject. Thus, for example, without having to frequently update the reference power ratio, it is accurately determined whether or not the measurement position of the physiological sound is appropriate, according to the change in physical characteristic.

Moreover, in the physiological sound examination device according to an aspect of the present invention, in the correction formula, a value obtained by multiplying a physical difference value between the first physical characteristic value and the second physical characteristic value by a predetermined coefficient may be added to the reference power ratio which is to be corrected.

With this, the reference power ratio is appropriately corrected according to the change in physical characteristic, by a simple calculation, for example.

Furthermore, in the physiological sound examination device according to an aspect of the present invention, in the correction formula, a correction difference value may be added to the reference power ratio, the correction difference value may indicate a difference between a first predicted power ratio and a second predicted power ratio, the first predicted power ratio may indicate a value predicted from the first physical characteristic value, using a prediction formula for predicting the power ratio from the physical characteristic value, and the second predicted power ratio may indicate a value predicted from the second physical characteristic value, using the prediction formula.

With this, even when there is no linear correlation between the power ratio and the physical characteristic value, for example, the reference power ratio is appropriately corrected according to the change in physical characteristic.

Moreover, in the physiological sound examination device according to an aspect of the present invention, each of the first physical characteristic value and the second physical characteristic value may represent one of a height, an age, a weight, a body surface area, and a body mass index.

With this, by using, for example, a characteristic which can be easily measured in an ordinary household, the reference power ratio is appropriately corrected according to the change in physical characteristic.

Furthermore, the physiological sound examination device according to an aspect of the present invention may further include an amplification unit which amplifies the second physiological sound using a value obtained by reversing a sign of the difference value.

With this configuration, the physiological sound measured at an inappropriate position can be approximated to the power of the physiological sound signal measured at an appropriate position, for example.

Moreover, in the physiological sound examination device according to an aspect of the present invention, the power calculation unit may (e) calculate, as the first power of the first physiological sound, power of the measured physiological sound in a first frequency band, and (f) calculate, as the second power of the second physiological sound, power of the measured physiological sound in a second frequency band different from the first frequency band, the power comparison unit may include: an extreme value detection unit which detects at least one pair of a first maximum value which is a maximum value in time-series data on the first power and a first time period including the first maximum value, and at least one pair of a second maximum value which is a maximum value in time-series data on the second power and a second time period including the second maximum value; and a coincident period detection unit which detects a coincident period which is coincident between the first time period and the second time period each of which is at least one in number, the power comparison unit may calculate the comparison result indicating a difference between the first maximum value and the second maximum value included in the coincident period, the difference indicating the difference between the first power and the second power, and the determination unit may determine that the measurement position of the physiological sound is inappropriate when the difference indicated by the comparison result is equal to or smaller than the threshold.

With this, each power (i.e., the first power and the second power) of the two kinds of physiological sounds which are obtained from the physiological sound measured at a certain position and are in different frequency bands is calculated.

Moreover, the coincident period where the first power and the second power have the respective maximum values at the similar time is detected. Furthermore, when the difference between the maximum values of the first power and the second power in the coincident period is equal to or smaller than the threshold, it is determined that the measurement position of the physiological sound is inappropriate.

To put it simply, when the maximum values of the first power and the second power in the coincident period are similar, it is determined, for example, that the maximum value of the first power is significantly influenced by the second power.

More specifically, when a physiological sound whose source is a certain organ is to be measured, the physiological sound examination device in this aspect can determine whether or not the measurement position of the physiological sound is appropriate based on whether or not the measured physiological sound is significantly influenced by a sound from another organ.

Furthermore, the physiological sound examination device according to an aspect of the present invention may further include a noise period detection unit which detects a low noise period which is included in a third frequency band of the physiological sound and in which power is equal to or smaller than a predetermined value, wherein the determination unit may determine that the measurement position is appropriate when the coincident period is not detected from the low noise period by the coincident period detection unit.

With this configuration, it is determined, in a short time with accuracy, whether the measurement position of the physiological sound is within the appropriate range, for example.

Moreover, the physiological sound examination device according to an aspect of the present invention may further include a display unit which displays an instruction, to the measurement subject or a measurer, to change the measurement position, when the determination unit determines that the measurement position is inappropriate.

With this configuration, when the measurement position is inappropriate, for example, the physiological sound examination device can instruct the measurement subject or the measurer to change the measurement position. Thus, more effective measurement support can be achieved.

Furthermore, in the physiological sound examination device according to an aspect of the present invention, the physiological sound may be to be measured at a predetermined position near a predetermined bone, and the display unit may display an instruction to move the measurement position to a direction away from the predetermined bone, when the determination unit determines that the measurement position is inappropriate.

With this configuration, when the measurement position is inappropriate, the measurer can correctly understand the direction to which the measurement position is to be changed, for example.

Moreover, in the physiological sound examination device according to an aspect of the present invention, the display unit may include at least one light emitting unit, and the at least one light emitting unit may display the instruction by emitting light, when the determination unit determines that the measurement position is inappropriate.

With this configuration, when the measurement position is inappropriate, the measurer can visually understand the direction to which the measurement position is to be changed, for example. More specifically, the physiological sound examination device allows the measurer to easily understand the instruction for the directional change.

Furthermore, the physiological sound examination device according to an aspect of the present invention may further include a direction detection unit which detects a predetermined direction, wherein the direction detection unit may detect, as the predetermined direction, a direction from an upper half of the living body to a lower half of the living body, when the determination unit determines that the measurement position is inappropriate, and the display unit may: include a plurality of light emitting units including the at least one light emitting unit; and cause one of the light emitting units to emit light, when the determination unit determines that the measurement position is inappropriate, the one of the light emitting units being located closest to the predetermined direction.

With this configuration, for example, the measurer can visually understand the direction to which the measurement position is to be changed and quickly find an appropriate position.

Moreover, in the physiological sound examination device according to an aspect of the present invention, the first frequency band may include a frequency component lower than a frequency component included in the second frequency band.

With this, for example, the accuracy of determining whether or not the measurement position is appropriate can be improved.

Furthermore, in the physiological sound examination device according to an aspect of the present invention, the third frequency band may include a frequency component of a lung sound at 1 kHz or lower.

With this, even when the measurement subject is breathing, it can be determined, in a short time with accuracy, whether or not the measurement position is appropriate.

Moreover, the present invention can be implemented as a physiological sound examination method including the characteristic processes executed by the physiological sound examination device in one of the above aspects. Furthermore, the present invention can be implemented as a computer program causing a computer to execute the characteristic processes included in the physiological sound examination method, and as a recording medium having the computer program recorded thereon. In addition, the computer program can be distributed via a transmission medium such as the Internet or via a recording medium such as a digital versatile disc (DVD).

Moreover, the present invention can be implemented as an integrated circuit including some or all of the components of the physiological sound examination device in one of the above aspects.

The present invention can provide a physiological sound examination device capable of accurately determining whether or not a measurement position of a physiological sound is appropriate.

For example, the physiological sound examination device according to an aspect of the present invention is capable of determining whether or not the measurement position of the physiological sound is at an inappropriate position which is too close to the bone such as clavicle or rib and whether or not the measurement position on the chest wall is inappropriate because a distance from the midline of the body is different from a specified distance.

BRIEF DESCRIPTION OF DRAWINGS

FIG. 22 is a flowchart showing an example of warning display processing performed when a measurement position of a physiological sound is determined to be inappropriate by a physiological sound examination device in Embodiment 5.

FIG. 23 is a diagram showing an example of a measurement position of the case where a warning light is turned on.

DETAILED DESCRIPTION OF INVENTION

The following is a description of embodiments according to the present invention, with reference to the drawings. It should be noted that components identical in the following embodiments are assigned the same numeral and, therefore, the explanation of these components may not be repeated.

Embodiment 1

Figure 1:
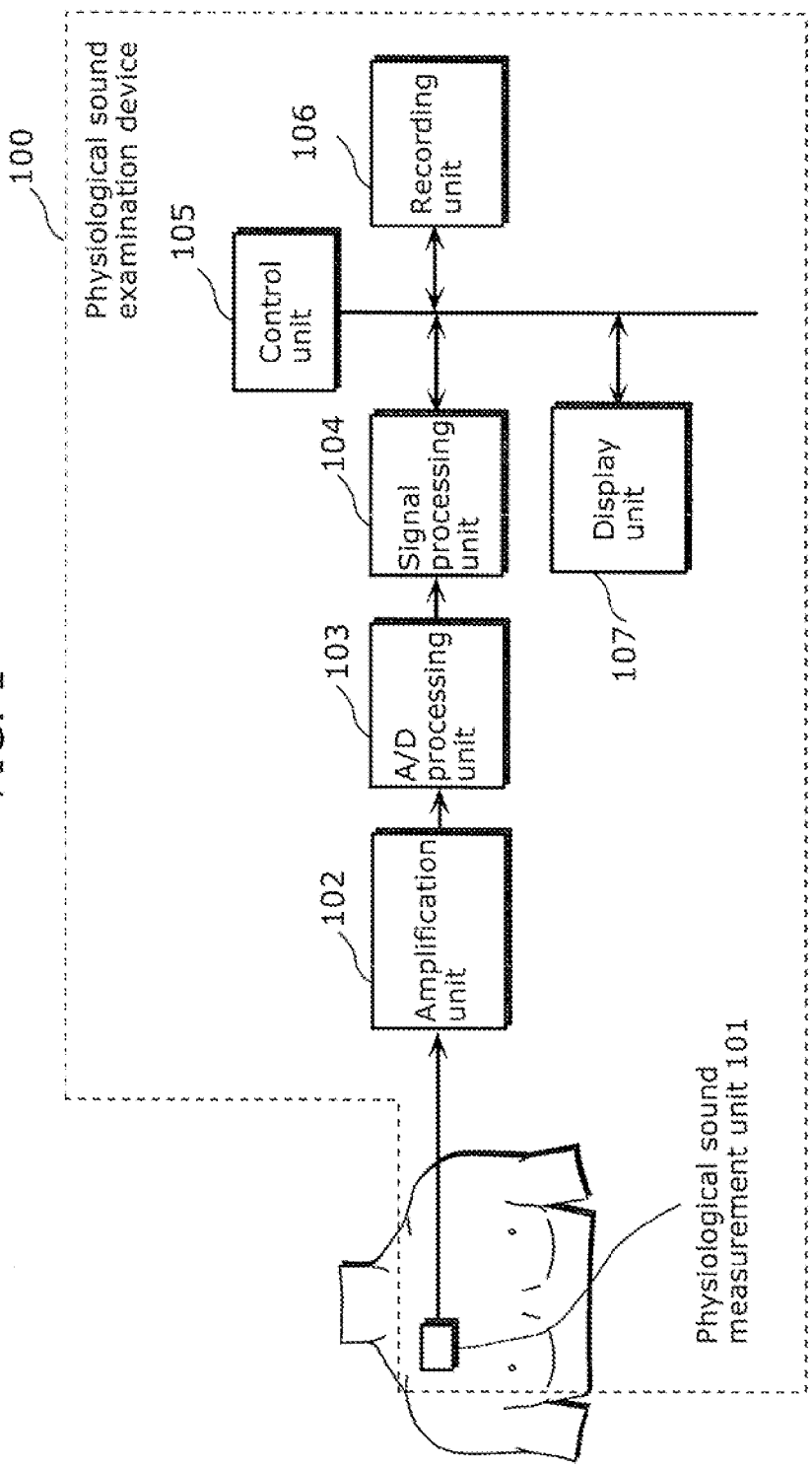
FIG. 1 is a diagram showing a basic configuration of a physiological sound examination device in Embodiment 1 according to the present invention.

FIG. 1 is a diagram showing a basic configuration of a physiological sound examination device 100 in Embodiment 1.

The physiological sound examination device 100 includes: a physiological sound measurement unit 101 which measures a physiological sound; an amplification unit 102 which amplifies a physiological sound signal measured by the physiological sound measurement unit 101; an A/D processing unit 103 which converts the physiological sound signal having been amplified by the amplification unit 102 into digital data; a signal processing unit 104 which analyzes the physiological sound signal having been converted into the digital data by the A/D processing unit 103; a control unit 105 which controls processing performed in the physiological sound examination device 100; a recording unit 106 which records information used by the signal processing unit 104 and a result of analyzing the physiological sound signal; and a display unit 107 which displays, to a measurer, the result of analyzing the physiological sound signal, a warning, and the like.

Firstly, a configuration of the physiological sound measurement unit 101 is described with reference to FIG. 2.

Figure 2:
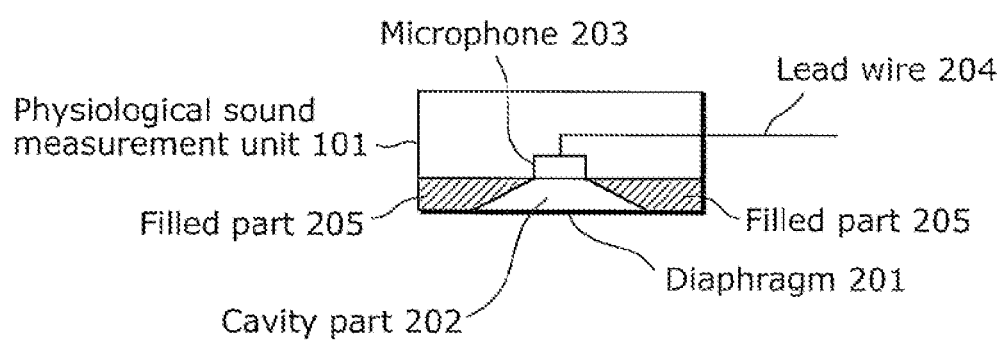
FIG. 2 is a diagram showing a schematic configuration of a physiological sound measurement unit in Embodiment 1.

FIG. 2 is a diagram showing a schematic configuration of the physiological sound measurement unit 101 in Embodiment 1.

As shown in FIG. 2, the physiological sound measurement unit 101 includes: a diaphragm part 201 which converts vibration of the physiological sound propagating through the body into air vibration; a cavity part 202 where the physiological sound having converted into the air vibration by the diaphragm part 201 propagates; a microphone 203 which converts the physiological sound propagated through the cavity part 202 into an electric signal; a lead wire 204 used for transmitting the physiological sound signal having been converted into the electric signal by the microphone 203; and a filled part 205.

It should be noted that a damping material, such as rubber or gel, is filled in the filled part 205 so that vibration from outside ambient noise does not propagate through the cavity part 202.

Next, a configuration of the signal processing unit 104 is described with reference to FIG. 3.

Figure 3:
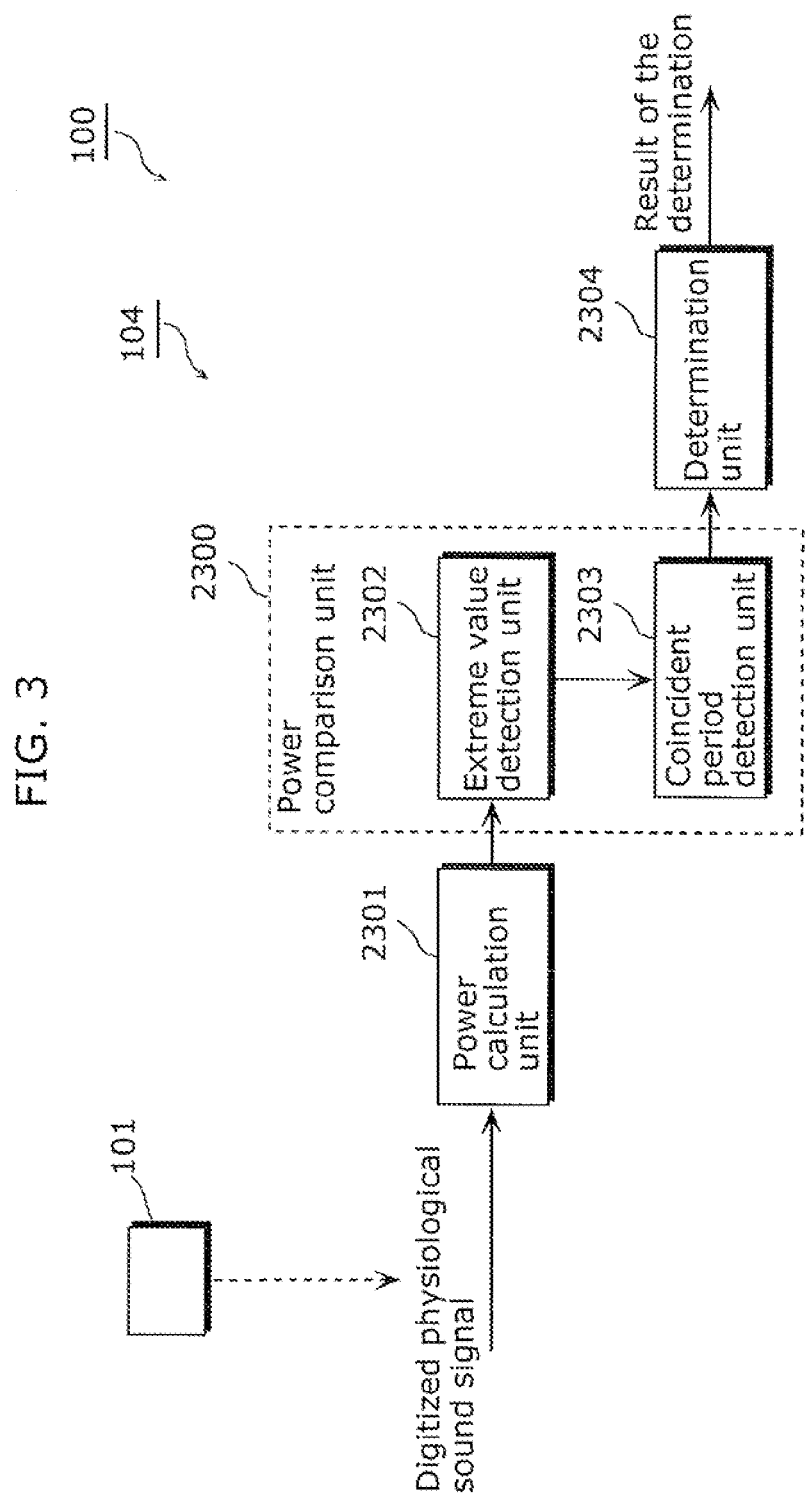
FIG. 3 is a diagram showing a basic configuration of a signal processing unit in Embodiment 1.

FIG. 3 is a block diagram showing a basic configuration of the signal processing unit 104 in Embodiment 1.

The signal processing unit 104 includes: a power calculation unit 2301 which calculates power for each of a first physiological sound and a second physiological sound that are two different kinds of sounds; a power comparison unit 2300 which compares the calculated powers (first power and second power) of the two kinds of physiological sounds; and a determination unit 2304 which determines whether or not a measurement position is appropriate, based on a difference between maximum values in a coincident period indicated by a result of the comparison performed by the power comparison unit 2300.

The power comparison unit 2300 includes: an extreme value detection unit 2302 which detects each extreme value in the time-series data on the calculated powers; and a coincident period detection unit 2303 which compares time periods each having the maximum value and then detects the coincident period.

It should be noted that the physiological sound examination device 100 in Embodiment 1 may include at least the physiological sound measurement unit 101, the power calculation unit 2301, the power comparison unit 2300, and the determination unit 2304, as shown in FIG. 3.

Figure 4:
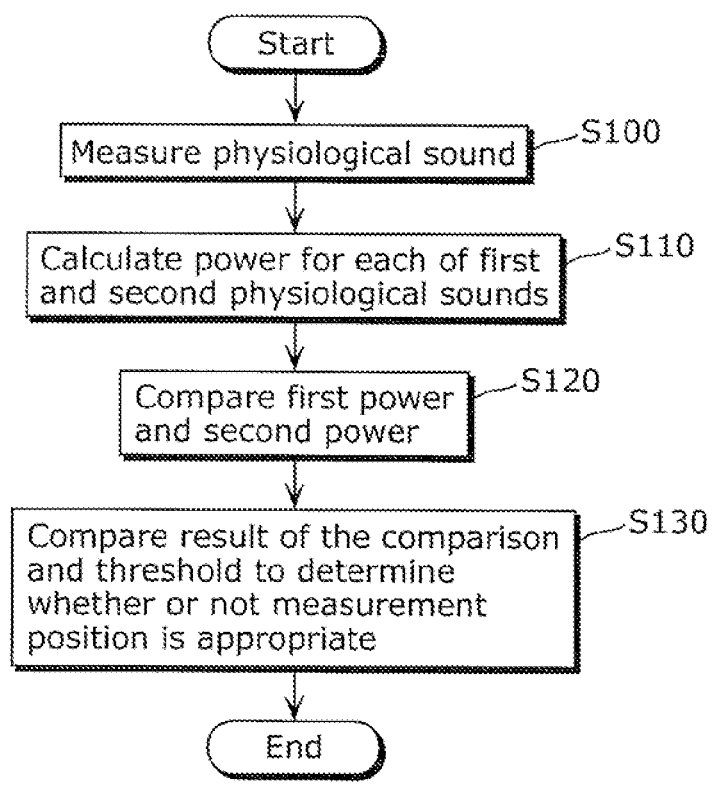
FIG. 4 is a flowchart showing an example of basic processing performed by the physiological sound examination device in Embodiment 1.

A flow of basic processing performed by the physiological sound examination device 100 configured as above is described, with reference to FIG. 4.

FIG. 4 is a flowchart showing an example of the basic processing performed by the physiological sound examination device 100 in Embodiment 1.

Note that basic processing performed by a physiological sound examination device 1300 in Embodiments 4 and 6 described later has the same flow as shown in FIG. 4.

The physiological sound measurement unit 101 measures a physiological sound originating from vibration propagating through inside the body of a measurement subject (S100).

The power calculation unit 2301 calculates the power (i.e., the first power) of the first physiological sound which is one of the two different kinds of sounds measured by the physiological sound measurement unit 101 and the power (i.e., the second power) of the second physiological sound which is the other one of the two different kinds of sounds (S110).

In the present embodiment, the power calculation unit 2301 calculates, as the first power, power in a first frequency band of the digitized physiological sound signal, and calculates, as the second power, power in a second frequency band of the digitized physiological sound signal.

The power comparison unit 2300 compares the first power and the second power obtained by the calculation, so as to calculate a comparison result indicating a ratio or a difference between the first power and the second power (S120).

In the present embodiment, the extreme value detection unit 2302 of the power comparison unit 2300 detects the maximum value in the time-series data for each of the first power and the second power (these maximum values are referred to as a first maximum value and a second maximum value). Moreover, the coincident period detection unit 2303 of the power comparison unit 2300 detects the coincident period which is coincident between a time period corresponding to the first maximum value and a time period corresponding to the second maximum value.

The power comparison unit 2300 further calculates a comparison result indicating a difference between the first maximum value and the second maximum value.

When the difference indicated by the comparison result is equal to or smaller than a threshold, the determination unit 2304 determines that the measurement position of the physiological sound is inappropriate (S130).

Figure 5:
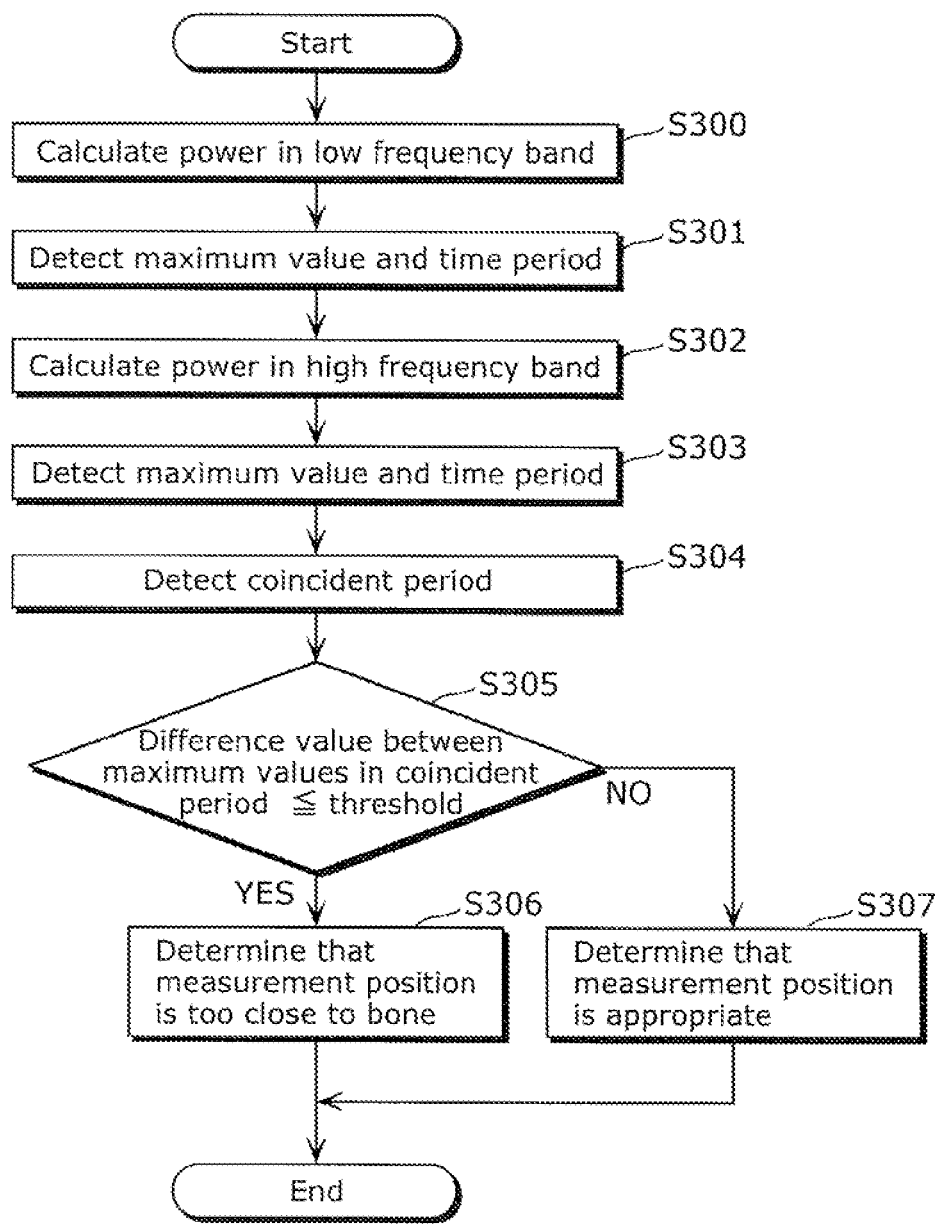
FIG. 5 is a flowchart showing an example of processing performed by the signal processing unit to determine whether or not a measurement position for the physiological sound measurement unit is appropriate.

The following describes a detailed operation performed when the physiological sound examination device 100 executing the above basic processing receives a physiological sound signal, with reference to FIG. 5.

FIG. 5 is a flowchart showing an example of processing performed by the signal processing unit 104 to determine whether or not a measurement position for the physiological sound measurement unit 101 is appropriate.

By this series of processing, a determination is made, for example, as to whether or not the measurement position is at an inappropriate position which is too close to the bone such as clavicle or rib.

Receiving the physiological sound signal from the A/D processing unit 103, the power calculation unit 2301 calculates power in a low frequency band out of a frequency band of a heart sound in order to extract a time period of the heart sound and an intensity of the heart sound (S300).

This low frequency band is an example of the first frequency band, and the physiological sound in the low frequency band is an example of the first physiological sound. Moreover, the power in the low frequency band is an example of the first power.

The power in the low frequency band is obtained by, for example, calculating power in a frame every 21 milliseconds, with one frame corresponding to 85 milliseconds.

Figure 6:
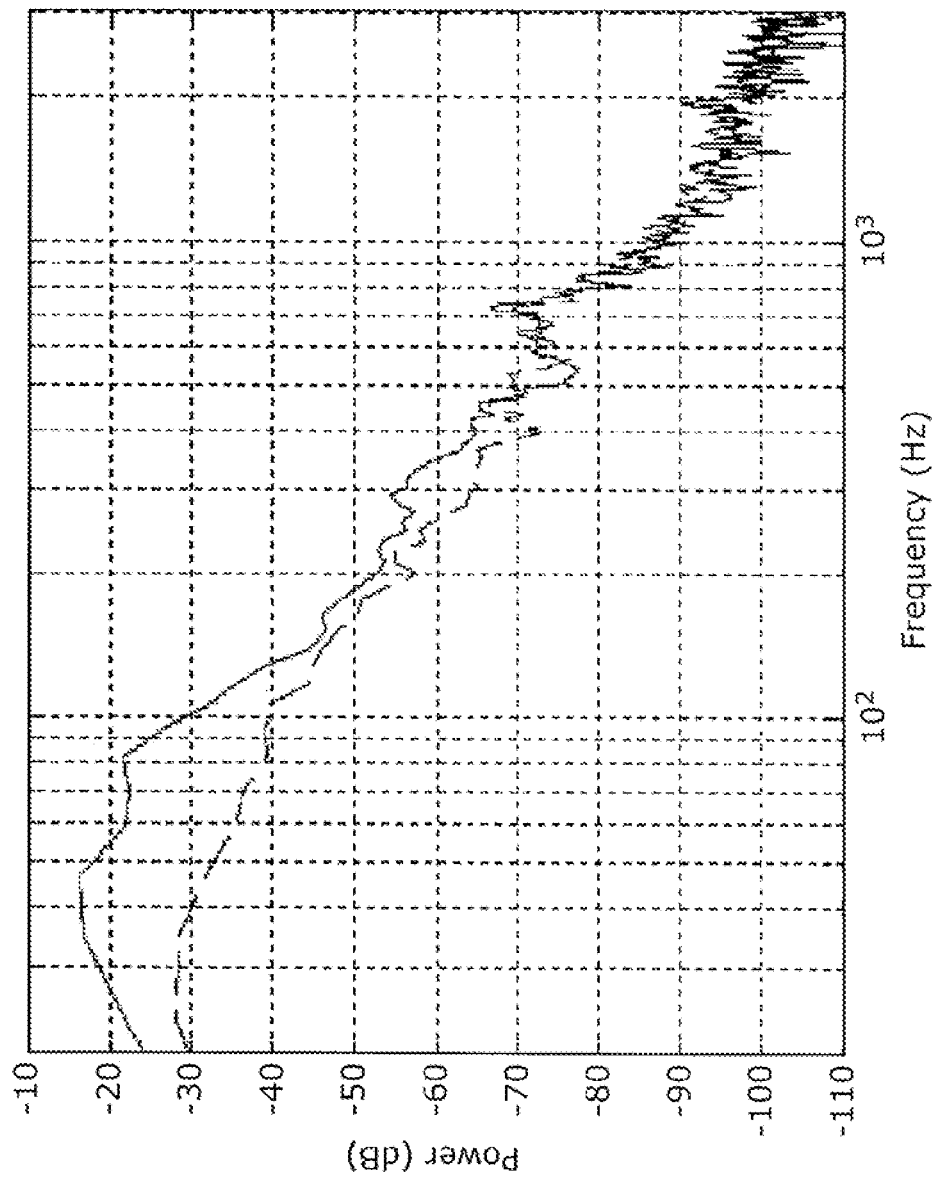
FIG. 6 is a diagram showing an example of a frequency response of a heart sound.

FIG. 6 is a diagram showing an example of a frequency response of a heart sound. A solid line indicates the heart sound, and a broken line indicates a background noise of when the heart sound is measured.

As shown in FIG. 6, spectral components of the heart sound are mostly included in a frequency band of not higher than 400 Hz. Thus, the frequency band for which the power is calculated may be any frequency band which is not higher than 400 Hz. In particular, it is desirable for the frequency band to be from 20 Hz to 80 Hz. This is because the time period and intensity of the heart sound are more likely to be detected from this frequency band with a high degree of accuracy.

Figure 7A:
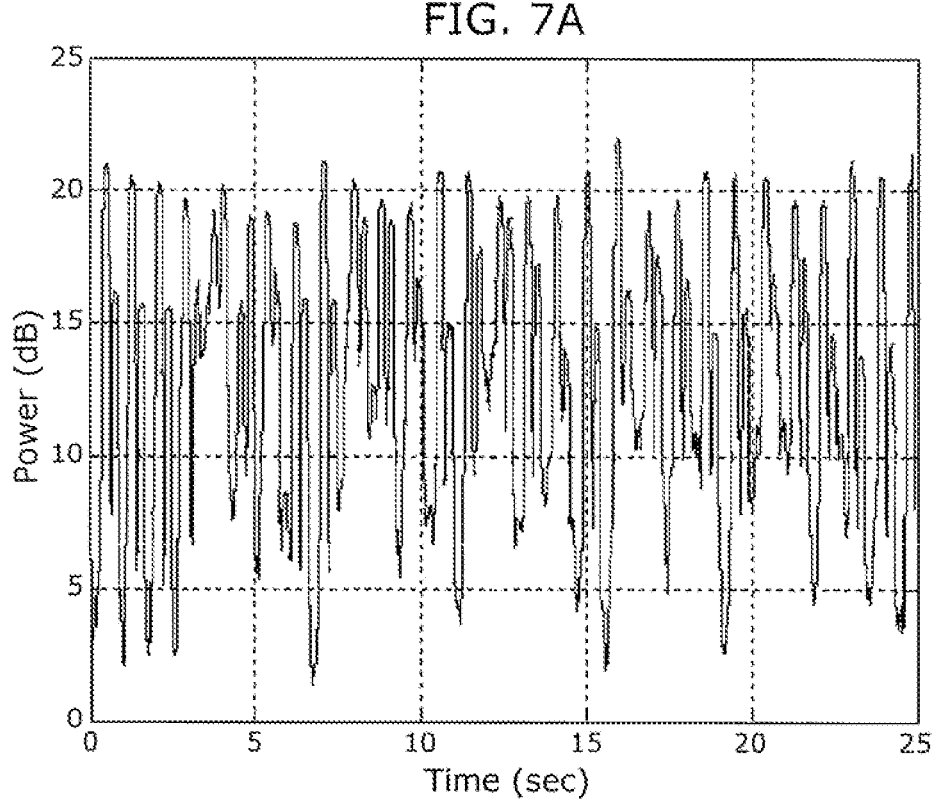
FIG. 7A is a diagram showing time-series data on power in a frequency band from 20 Hz to 80 Hz of a physiological sound signal measured around the clavicle.

FIG. 7A shows time-series data on the power in a frequency band from 20 Hz to 80 Hz of a physiological sound signal measured around the clavicle.

In FIG. 7A, a I sound and a II sound of the heart sound appear as power peaks. The I sound refers to a sound generated at the beginning of a ventricular systole whereas the II sound refers to a sound generated at the beginning of a ventricular diastole. In FIG. 7A, for example, a power peak of slightly more than 20 dB which appears immediately after the start of the measurement is the I sound, and a power peak of slightly more than 15 dB which appears immediately after this I sound is the II sound. Then, the I sound and the II sound alternate. It should be noted that the power levels of the I and II sounds vary from one individual to another, and may vary within the same individual.

Next, the extreme value detection unit 2302 detects a maximum value and a time period which includes the current maximum value, from the time-series data on the power calculated in S300 for the low frequency band of the heart sound (S301). The maximum value and the time period including the current maximum value are detected from a time period where the I or II sound of the heart sound appears.

These detected maximum value and time period are examples of the first maximum value and a first time period, respectively. Here, at least one maximum value and a time period including the current maximum value are detected.

Suppose, for example, that an appearance time of the I and II sounds corresponds to a length of five frames. In this case, the time period to be detected refers to this five-frame time period, and the maximum value refers to the largest value among values representing the five powers calculated for these frames.

The maximum value is detected as follows. When the time-series data on the power is differentiated in the direction of the time axis and power at a time where a differentiated value changes from positive to negative is equal to or larger than a predetermined value, this power is detected as the maximum value (referred to as the "low-frequency maximum value" hereafter).

The predetermined value may be an average value of the powers in the time-series data for ten seconds before the time at which the differentiated value changes from positive to negative, or may be a value calculated by subtracting 10 dB from the largest value. Moreover, the predetermined value is not limited to this, and may be a value which is not less than the minimum value and not more than the maximum value in the time-series data on the power before the time at which the differentiated value changes from positive to negative.

It should be noted that when a plurality of low-frequency maximum values are detected in a short time period, the low-frequency maximum value which is a local maximum value is selected.

The time period which includes the low-frequency maximum value is detected as follows. Minimum values of power are detected from the time-series data, and times of the minimum values before and after the low-frequency maximum value are respectively detected as a start time and an end time of the current time period.

The minimum value is detected as follows. When the time-series data on the power is differentiated in the direction of the time axis and power at a time where a differentiated value changes from negative to positive is equal to or smaller than a predetermined value, this power is detected as the minimum value. Note that the maximum value and the minimum value may be detected by other methods.

Figure 7B:
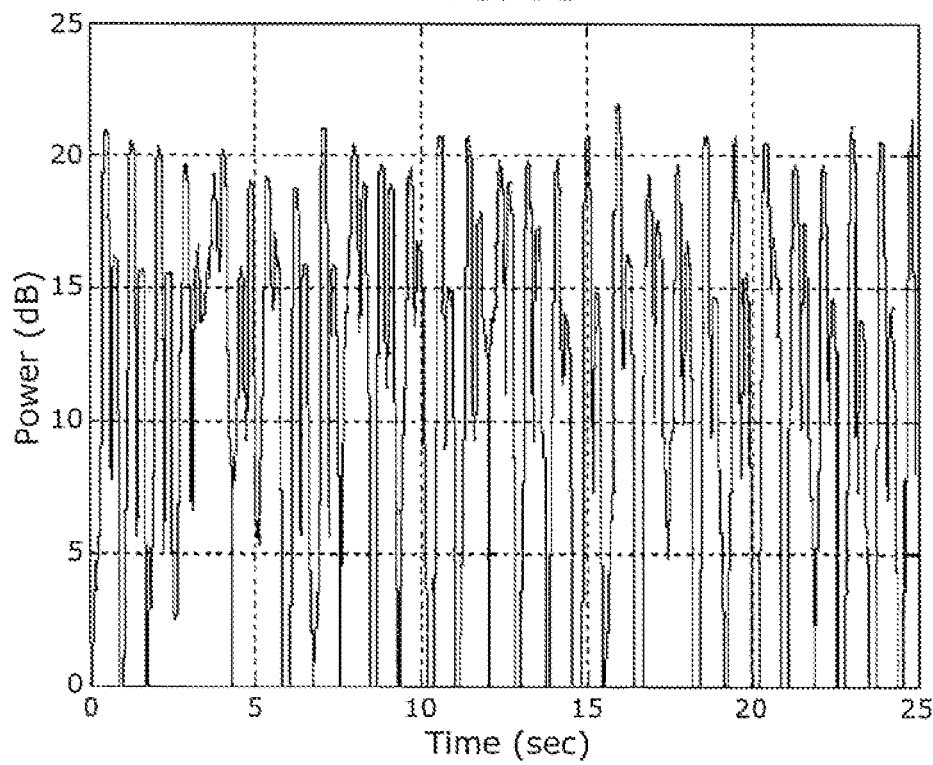
FIG. 7B is a diagram showing time-series data obtained by detecting, from the data shown in FIG. 7A, a maximum value in the low frequency band of the heart sound and a time period including the maximum value, and by masking values of the other time periods with zero.

FIG. 7B is a diagram showing time-series data obtained by detecting, from the data shown in FIG. 7A, the low-frequency maximum value and the time period including this low-frequency maximum value, and by masking the values of the other time periods with zero.

The power calculation unit 2301 calculates power in a high frequency band out of the frequency band of the heart sound, using the physiological sound signal received from the A/D processing unit 103 (S302).

The spectral components of the heart sound are mostly included in the frequency band of not higher than 400 Hz. Thus, the frequency band for which the power is calculated may be any frequency band which is not higher than 400 Hz, and may include a frequency band larger than the frequency band (from 20 Hz to 80 Hz) used for calculating the power in S300.

In particular, it is desirable for the frequency band to be from 300 Hz to 400 Hz. In the case of bone conduction via ribs, clavicle, or the like, the heart sound in the frequency band from 300 Hz to 400 Hz propagates without being so much attenuated. However, when the heart sound propagates through tissues other than the bones, such as muscles, fat, or lungs, the sound is attenuated significantly as compared with the case of bone conduction.

On account of this, a power difference in the heart sound is apparent in this frequency band between around clavicles and other areas. Therefore, on the basis of this frequency band, the appropriateness of the measurement position of the physiological sound is more likely to be determined with a high degree of accuracy.

It should be noted that this frequency band (i.e., the high frequency band) is an example of the second frequency band, and the physiological sound in the high frequency band is an example of the second physiological sound. Moreover, note that the power in the high frequency band is an example of the second power.

As can be understood, the first frequency band includes a frequency component lower than a frequency component included in the second frequency band, in the present embodiment.

Figure 8A:
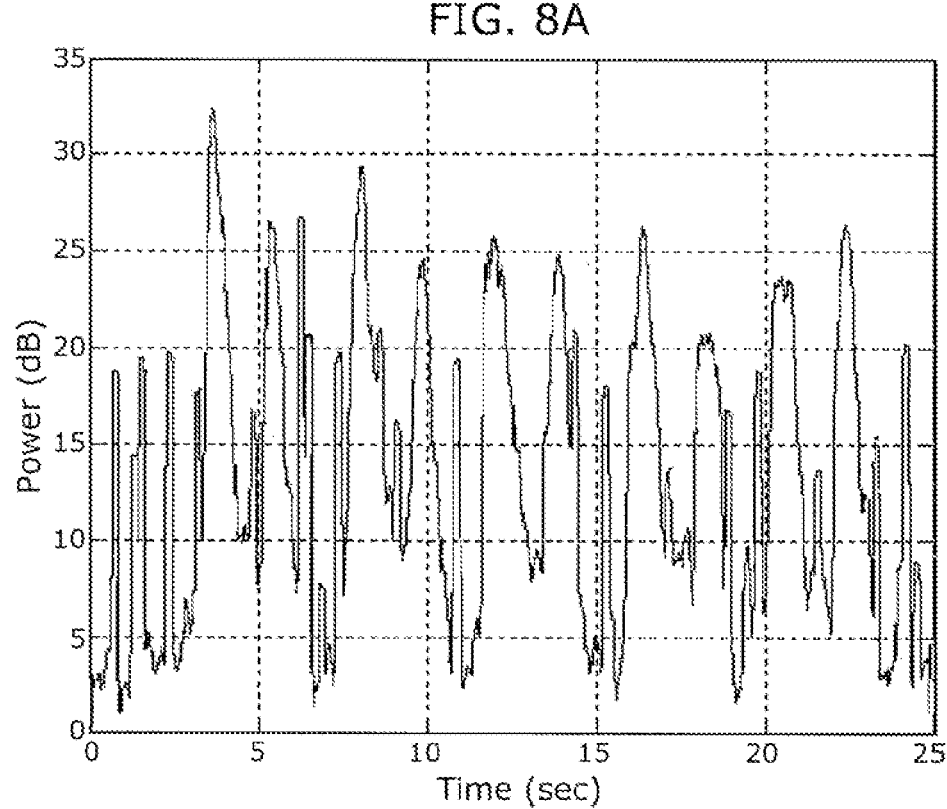
FIG. 8A is a diagram showing time-series data on power in a frequency band from 300 Hz to 400 Hz of a physiological sound signal measured around the clavicle.

FIG. 8A is a diagram showing time-series data on power in a frequency band from 300 Hz to 400 Hz of a physiological sound signal measured around the clavicle. The data shown in FIG. 8B includes power peaks of the heart sound and power rises of the lung sound of during breathing.

To put it simply, the physiological sound in the low frequency band measured in S300 is mainly the heart sound, and the physiological sound in the high frequency band measured in S302 is a mixed sound including mainly the heart sound and the lung sound.

From the time-series data on the power of the heart sound in the high frequency band calculated in S302, the extreme value detection unit 2302 detects a maximum value (may be referred to as the "high-frequency maximum value" hereafter) and a time period which includes the current high-frequency maximum value (S303).

These detected high-frequency maximum value and time period are examples of the second maximum value and a second time period, respectively. Here, the extreme value detection unit 2302 detects at least one pair of the high-frequency maximum value and the time period including the current high-frequency maximum value.

Figure 8B:
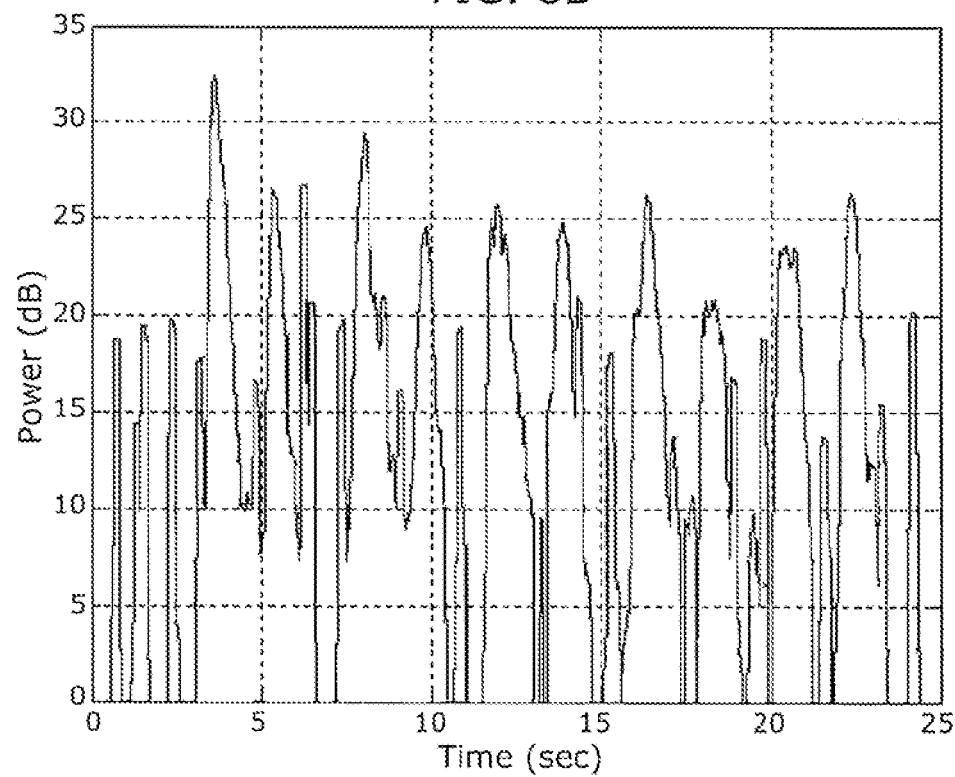
FIG. 8B is a diagram showing time-series data obtained by detecting, from the data shown in FIG. 8A, a maximum value in the high frequency band of the heart sound and a time period including the maximum value, and by masking values of the other time periods with zero.

A detection method in S303 may be the same as used above in S301. FIG. 8B is a diagram showing time-series data obtained by detecting, from the data shown in FIG. 8A, the high-frequency maximum value and the time period, and by masking the values of the other time periods with zero.

The coincident period detection unit 2303 compares at least one time period detected in S301 and at least one time period detected in S303 to detect a coincident period which is coincident between these time periods (S304).

To be more specific, the time period is detected, between the time-series data on the low frequency band and the time-series data on the high frequency band, in which upward and downward curves of powers having the respective maximum values as the peaks are present at the same or similar time.

It should be noted that in the detection of the coincident period, that is, in the determination as to whether or not the time periods including the respective maximum values coincide with each other between the times-series data on the low frequency band and the time-series data on the high frequency band, start or end times of the in periods do not necessarily need to be identical to each other and may be different by a predetermined value or smaller.

Since the peaks of the I and II sounds of the heart sound need to be understood as corresponding to respective time periods different from each other, it is desirable for this predetermined value to be 300 milliseconds or smaller.

Figure 9A:
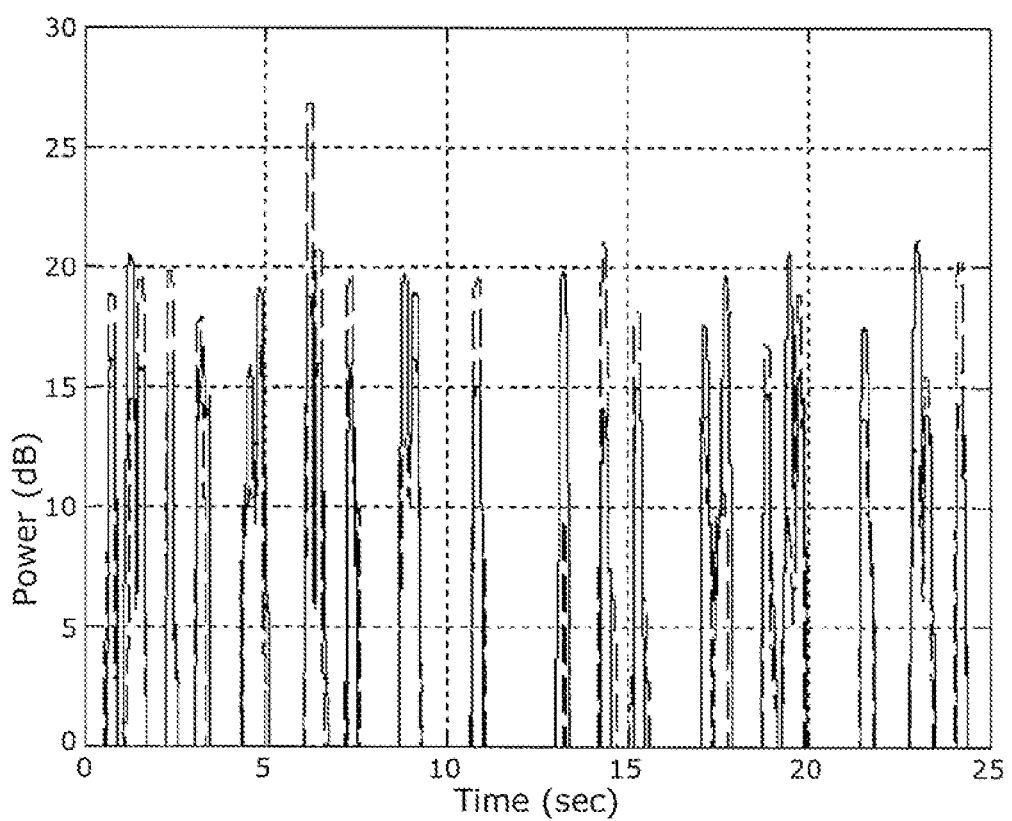
FIG. 9A is a diagram showing coincident periods detected using the time-series data shown in FIG. 7B and FIG. 8B.

FIG. 9A is a diagram showing the coincident periods detected using the time-series data shown in FIG. 7B and FIG. 8B. Note that the time periods other than the detected coincident periods are masked by zero. A solid line indicates the power in the time period corresponding to the low-frequency maximum value, and a broken line indicates the power in the time period corresponding to the high-frequency maximum value.

Figure 9B:
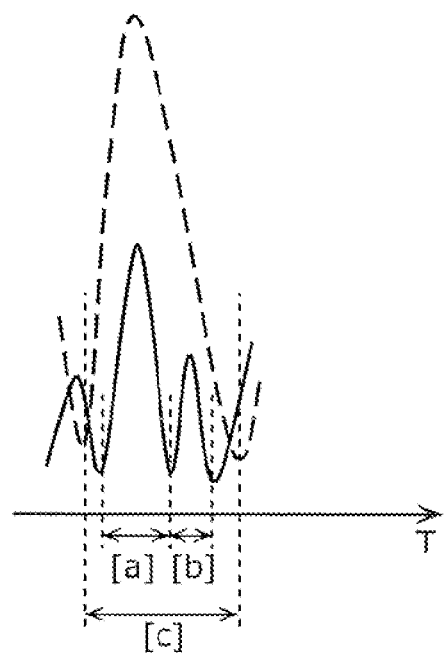
FIG. 9B is a diagram showing an example of a part which is not detected as a coincident period in the time-series data on the powers in the low and high frequency bands.
Figure 9C:
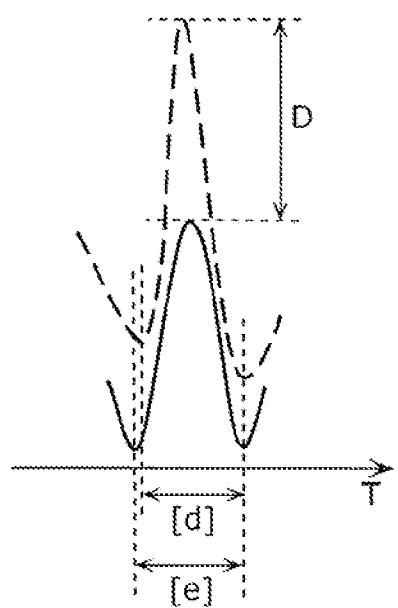
FIG. 9C is a diagram showing an example of a part which is detected as the coincident period in the time-series data on the powers in the low and high frequency bands.

Here, the coincident period is described briefly, with reference to FIG. 9B and FIG. 9C.

FIG. 9B is a diagram showing an example of a part which is not detected as a coincident period in the time-series data on the powers in the low and high frequency bands.

FIG. 9C is a diagram showing an example of a part which is detected as the coincident period in the time-series data on the powers in the low and high frequency bands.

As shown in FIG. 9B, time periods [a] and [b] both corresponding to the low-frequency maximum values are included in a time period [c] corresponding to the high-frequency maximum value. However, the start and end times of each of the time periods [a] and [b] are significantly different from the start and end times of the time period [c]. Thus, the coincident period detection unit 2303 does not detect any of the time periods [a], [b], and [c] as the coincident period.

As shown in FIG. 9C, the start and end times of a time period [d] corresponding to the low-frequency maximum value are extremely close to, not exactly the same though, the start and end times of a time period [e] corresponding to the high-frequency maximum value (For example, a difference is equal to or smaller than the predetermined value defined regarding the coincide period). Thus, the coincident period detection unit 2303 detects the time period [d] or [e] as the coincident period.

Here, since the time period [c] does not coincide with the time periods [a] and [b] in FIG. 9B, the time period [c] is regarded as the time period corresponding to a change in the lung sound of during breathing.

On the other hand, the time period [d] can be said to coincide with the time period [e] in FIG. 9C. This coincidence is thought to take place by accident or because the spectral component of the high frequency band is influenced by the heart sound.

More specifically, suppose that a difference ("D" in FIG. 9C, for example) between the high-frequency maximum value and the low-frequency maximum value in the coincident period is relatively small. In such a case, it is presumed that the high-frequency band is influenced by the heart sound by bone conduction because the measurement position of the physiological sound is located at an inappropriate position which is too close to the bone such as clavicle or rib.

Thus, when the difference between the low-frequency maximum value and the high-frequency maximum value in the coincident period is equal to or smaller than a predetermined threshold, the determination unit 2304 determines that the measurement position is inappropriate. A specific processing flow is as follows.

The power comparison unit 2300 calculates the difference between the low-frequency maximum value and the high-frequency maximum value in the coincident period detected in S304 by, for example, subtracting the high-frequency maximum value from the low-frequency maximum value. Then, the determination unit 2304 compares the calculated difference value with the predetermined threshold (S305).

When the difference value is equal to or smaller than the predetermined threshold (Yes in S305), the determination unit 2304 determines that the measurement position is inappropriate because the position is too close to the bone such as clavicle or rib (S306).

Then, the control unit 105 warns the measurer, using the display unit 107, that the measurement position of the physiological sound is too close to the bone.

When the difference value is larger than the predetermined threshold (No in S305), the determination unit 2304 determines that the measurement position is appropriate (S307).

For example, when the predetermined threshold is 5 dB and "D" shown in FIG. 9C is 5 dB or smaller, that is, when the difference value D corresponding to the coincident period ([d] or [e]) is equal to or smaller than the predetermined threshold, the measurement position of the physiological sound is determined to be inappropriate because the position is too close to the clavicle.

It should be noted that, when a plurality of coincident periods are detected as shown in FIG. 9A, the determination unit 2304 may determine the measurement position to be inappropriate when the difference value in at least one time period is equal to or smaller than the predetermined threshold. With this, for example, when the measurement position is not appropriate actually, the measurement position is reliably determined to be inappropriate.

For example, when each of the difference values of a predetermined number or more of coincident periods is equal to or smaller than the predetermined threshold, the determination unit 2304 may determine that the measurement position is inappropriate. This can, for example, prevent a determination error caused due to some kind of entered noise.

The predetermined threshold varies according to the microphone used. However, a value adequate to discriminate between an inappropriate measurement position and an appropriate measurement position may be obtained experimentally or logically, and this obtained value may be used as the threshold.

It should be noted that, when the power of the corresponding frequency band is calculated in each of S300 and S302, the power of a physiological sound signal passing through a band-pass filter corresponding to the respective frequency band may be used. Moreover, frequency conversion may be performed on the physiological sound signal received from the A/D processing unit 103, and the power of the corresponding frequency band may be calculated from the power spectrum of the physiological sound signal.

Figure 10A:
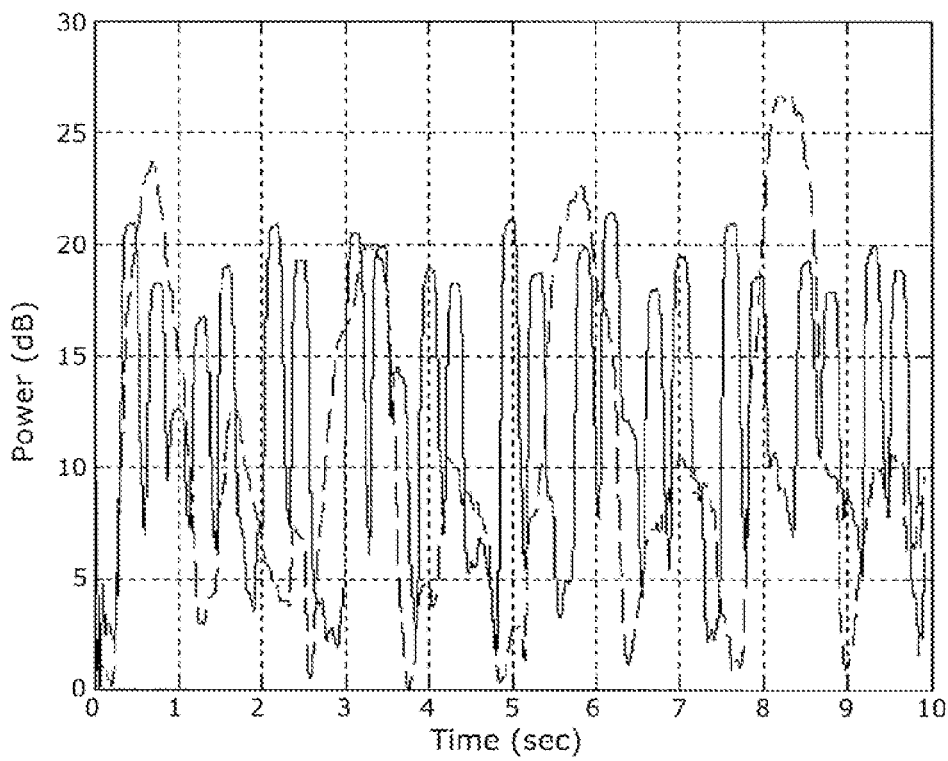
FIG. 10A is a diagram showing an example of time-series data on a low-frequency power and a high-frequency power of a physiological sound measured on the chest wall.
Figure 10B:
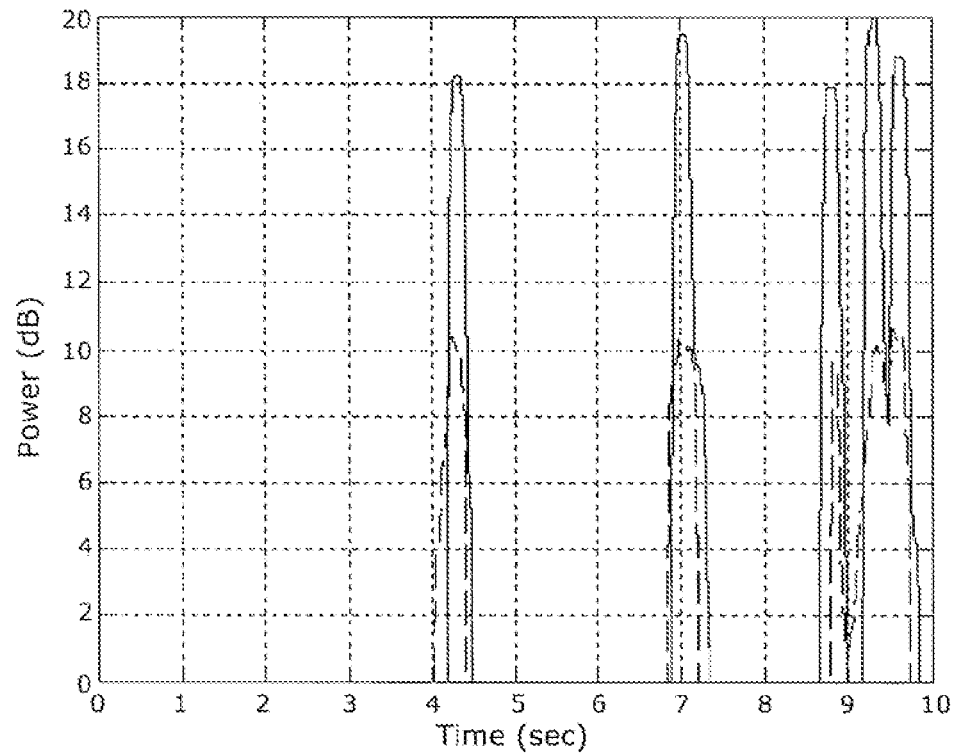
FIG. 10B is a diagram showing coincident periods detected from the data shown in FIG. 10A.

FIG. 10A and FIG. 10B show data on the physiological sound signal measured at the second intercostal space on the right midclavicular line.

To be more specific, in FIG. 10A, a solid line indicates the time-series data on the power in the frequency band from 20 Hz to 80 Hz whereas a broken line indicates the time-series data on the power in the frequency band from 300 Hz to 400 Hz. FIG. 10B shows the coincident periods obtained by performing the above processes from S300 to S304. A solid line indicates the power in the frequency band from 20 Hz to 80 Hz whereas a broken line indicates the power in the frequency band from 300 Hz to 400 Hz.

When the physiological sound is measured on the chest wall, the heart sound is attenuated while propagating through the lungs. In particular, since the lungs have characteristics like a low-pass filter, the power of the heart sound in the high frequency band is attenuated significantly as compared with the power in the low frequency band.

On this account, as shown in FIG. 10B, a difference between the low-frequency maximum value and the high-frequency maximum value is large. For example, when the predetermined threshold is 5 dB, the difference value in each of the coincident periods shown in FIG. 10B is larger than the predetermined threshold in S305. As a result, the measurement position is determined to be appropriate in S307.

As described thus far, the physiological sound examination device 100 is capable of determining, by using the heart sound included in the measured physiological sound, whether or not the measurement position of the physiological sound is at an inappropriate position which is too close to the bone such as clavicle or rib.

It should be noted that although the present embodiment describes that the physiological sound measurement unit 101 transmits the physiological sound signal via the lead wire 204, the present invention is not limited to this. The physiological sound signal may be transmitted by a radio transmitter instead of the lead wire 204.

With this configuration, the lead wire 204 is unnecessary. This can prevent, for example, noise from entering from the lead wire 204. Here, the noise is caused by vibration from, for example, contact between the lead wire 204 and the body or by the influence of electromagnetic waves or the like.

Moreover, the physiological sound examination device 100 may start analyzing the physiological sound to diagnose a disease only when the measurement position is determined to be appropriate. With this configuration, it is always assured that the lung sound to be examined by the physiological sound examination device 100 is a physiological sound measured at the correct position. This means that when the doctor examines the result of analyzing the physiological sound to diagnose, the diagnosis can be made using the highly reliable result of the lung sound analysis.

Although the physiological sound measurement unit 101 uses the microphone 203 to detect the physiological sound, the physiological sound may be detected using an acceleration sensor. In this case, the diaphragm part 201 and the cavity part 202 are unnecessary. This can reduce the possibility that the ambient noise propagating by air vibration is mixed into the physiological sound via the diaphragm 201 or the cavity part 202.

Since the present embodiment assumes that the power of the physiological sound is expressed in decibels using a natural logarithm, the difference between the maximum values is calculated by subtraction. However, when the difference between the maximum values is not calculated using a natural logarithm, the calculation is performed by division or bit shift operation.

Supplementary notes described above for Embodiment 1 are applied to the following other embodiments as well.

Embodiment 2

Figure 11:
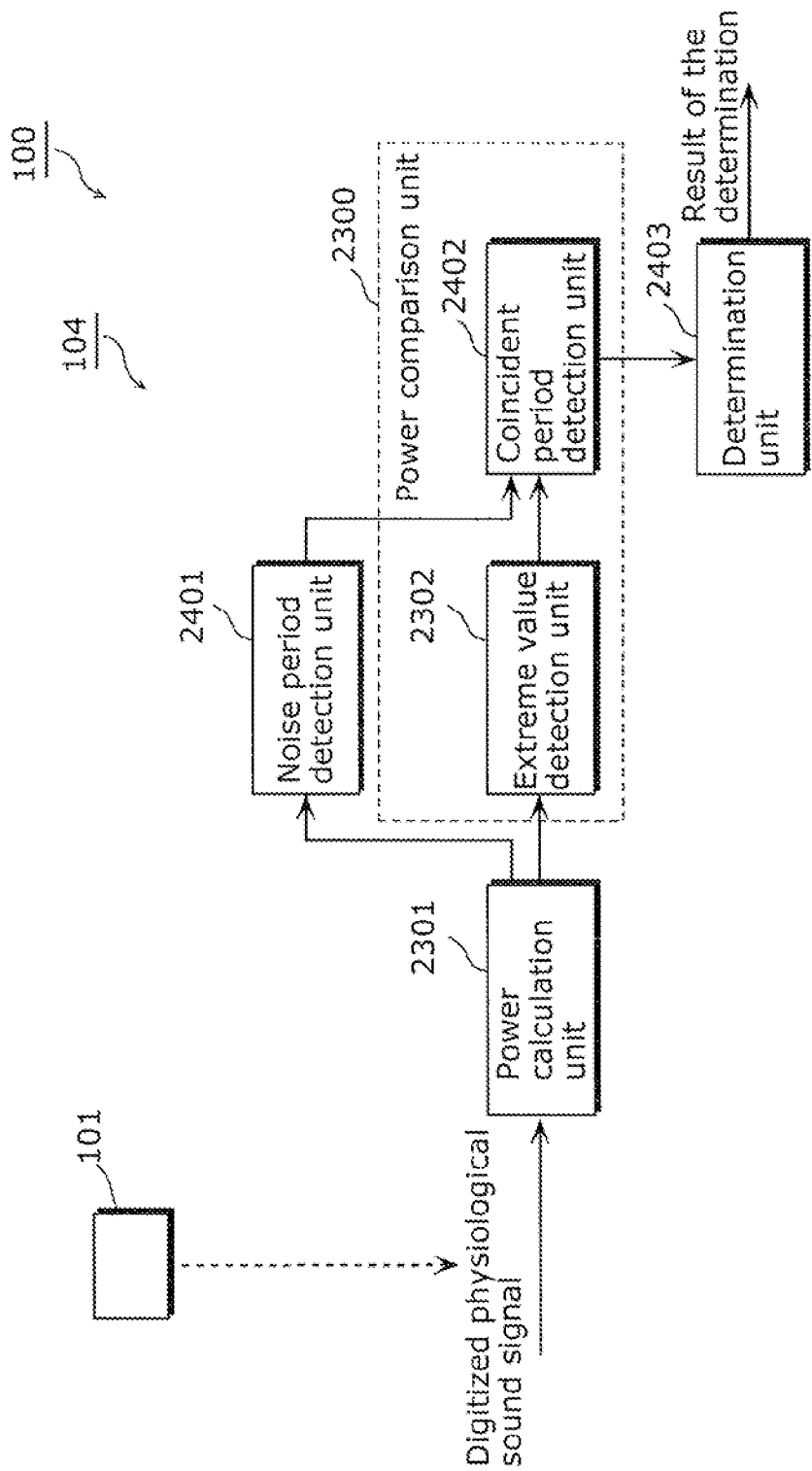
FIG. 11 is a diagram showing a basic configuration of a signal processing unit in Embodiment 2.
Figure 12:
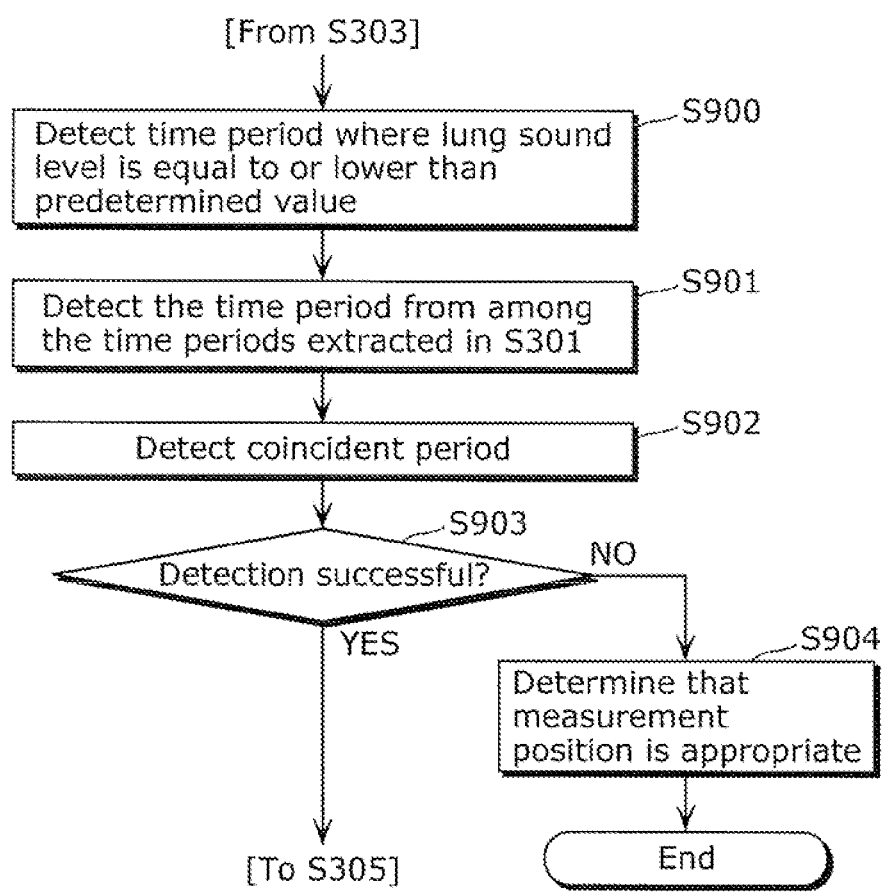
FIG. 12 is a flowchart showing an example of processing performed by the physiological sound examination device to detect a coincident period in Embodiment 2.

FIG. 11 is a block diagram showing a basic configuration of the signal processing unit 104 included in the physiological sound examination device 100 in Embodiment 2. FIG. 12 is a flowchart showing an example of processing performed by the physiological sound examination device 100 to detect a coincident period in Embodiment 2.

In the following, components identical to those in Embodiment 1 are assigned the same numerals used in Embodiment 1 and, therefore, the explanation of these components may be omitted.

A noise period detection unit 2401 detects a low noise period where a lung sound level is low, from the power of the physiological sound calculated by the power calculation unit 2301 (S900).

Figure 13:
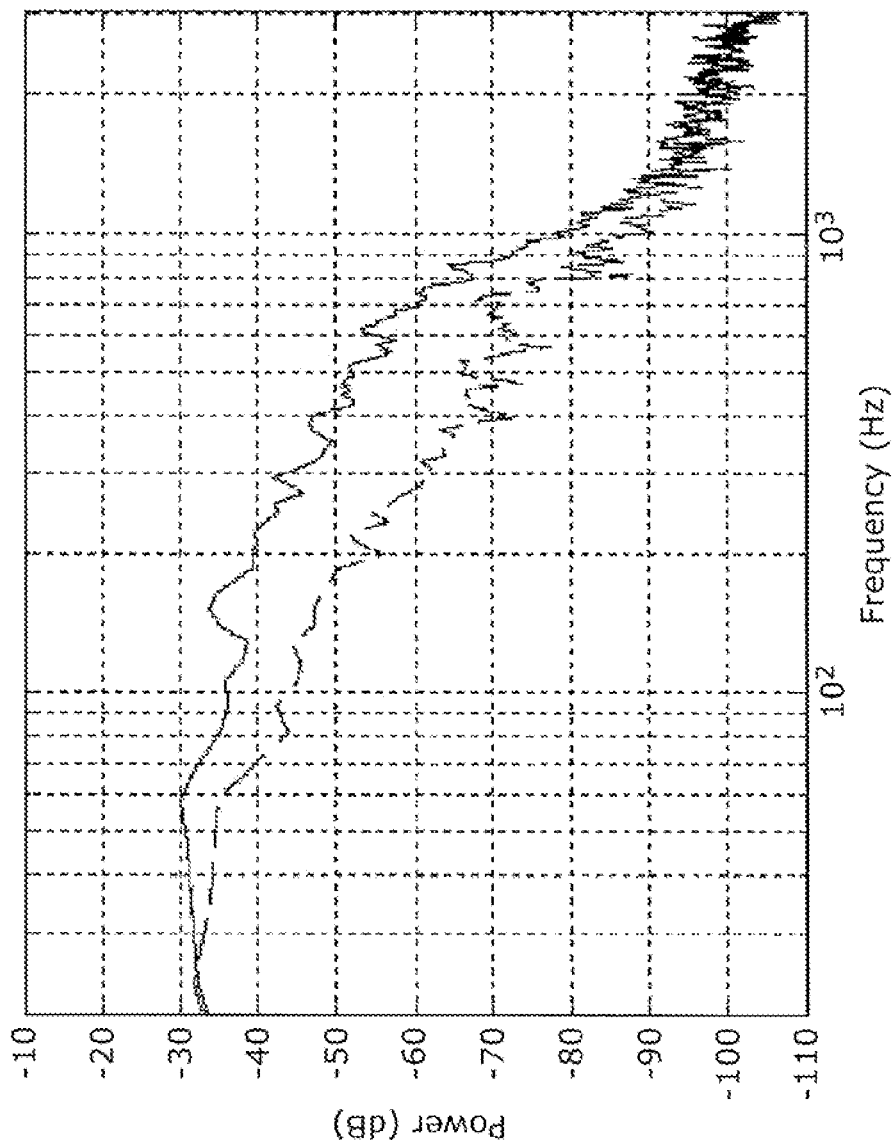
FIG. 13 is a diagram showing an example of a frequency response of a lung sound measured on the chest wall.

FIG. 13 is a diagram showing an example of a frequency response of a lung sound measured on the chest wall. As shown in FIG. 13, spectral components of the lung sound are mostly included in a frequency band of not higher than 1 kHz. Here, as shown in FIG. 6, many spectral components of the heart sound appear particularly in the frequency band of not higher than 100 Hz.

Thus, the power calculation unit 2301 calculates the power included in a frequency band from 100 Hz to 1 kHz. The noise period detection unit 2401 detects, as the low noise period, a time period where the power calculated by the power calculation unit 2301 is equal to or smaller than a predetermined value. It should be noted that a band including frequency components of the lung sound at 1 kHz or lower is an example of a third frequency band.

The noise period detection unit 2401 detects a time period included in the low noise period, from among a plurality of time periods detected in S301 each of which includes the maximum value of the low frequency band (i.e., the low-frequency maximum value) (S901). As a result, a heart sound period is detected in the low noise period where the lung sound level is low.

A coincident period detection unit 2402 detects a time period coincident between the time period detected in S901 and the time period detected in S303 (S902).

As a result, the coincident period detection unit 2402 detects, as the coincident period, the time period which is included in the time period where the lung sound level is low and which shows the power at a high level in each of the low and high frequency bands of the heart sound.

A determination unit 2403 determines whether or not the detection of the coincident period in S902 is successful (S903). When determining in S903 that the detection of the coincident period is successful (Yes in S903), the determination unit 2403 performs S305 and the subsequence processes.

Moreover, when determining that the detection of the coincident period is unsuccessful (No in S903), the determination unit 2403 determines that the measurement position is at an appropriate position which is not too close to the bone such as clavicle or rib (S904).

Since the high frequency band of the heart sound overlaps with the frequency band of the lung sound, the spectral components of the heart sound may be masked by the spectral components of the lung sound during a respiratory period. Therefore, the time period coincident between the low and high frequency bands of the heart sound can be detected more easily in the time period where the lung sound level is low.

Suppose that the power of the heart sound in the low frequency band is large and the power of the heart sound in the high frequency band is small, even in the time period where the lung sound level is low. In such a case, it is unlikely that the heart sound enters the sensor by bone conduction. Accordingly, the measurement position can be determined not to be too close to the bone.

By using the heart sound in the time period where the lung sound level is low, time taken after the start of the measurement to determine whether or not the measurement position is appropriate can be reduced.

For example, as in the flowchart shown in FIG. 5, suppose that the appropriateness of the measurement position is determined after the detection of the coincident period without consideration of the low noise period where the lung sound level is low. In this case, when the signal is a physiological sound signal as shown in FIG. 10A, the determination as to the appropriateness can be made only after at least about four seconds after the start of the measurement (see FIG. 10B).

However, as can be seen from the solid line in FIG. 10A, the power of the heart sound in the low frequency band increases around after two seconds after the start of the measurement. Moreover, as can be seen from the broken line in FIG. 10A, the lung sound level decreases with no power increase.

Accordingly, in S901, this time period is detected to have the low-frequency maximum value in the low noise period. However, this time period is not detected as the coincident period since the power shown by the broken line is small and the high-frequency maximum value is not detected. In other words, it is determined in S903 that the detection of the coincident period is unsuccessful. As a result, in S904, the measurement position is determined to be appropriate.

In this way, the determination as to the appropriateness of the measurement position is made within about two seconds after the start of the measurement. This means that, for example, without placing too much burden on the measurement subject, the measurer can ask the measurement subject to hold breath until the end of the determination as to whether the physiological sound is appropriate. As a consequence of this, the determination can be made in a shorter time as well.

As described thus far, the physiological sound examination device 100 can accurately determine in a short time, by using the low noise period, whether or not the measurement position of the physiological sound is too close to the bone such as clavicle or rib.

It should be noted that, the physiological sound examination device 100 in Embodiment 2 may include at least the physiological sound measurement unit 101, the power calculation unit 2301, the power comparison unit 2300, the noise period detection unit 2401, and the determination unit 2403, as shown in FIG. 11.

Embodiment 3

Figure 14:
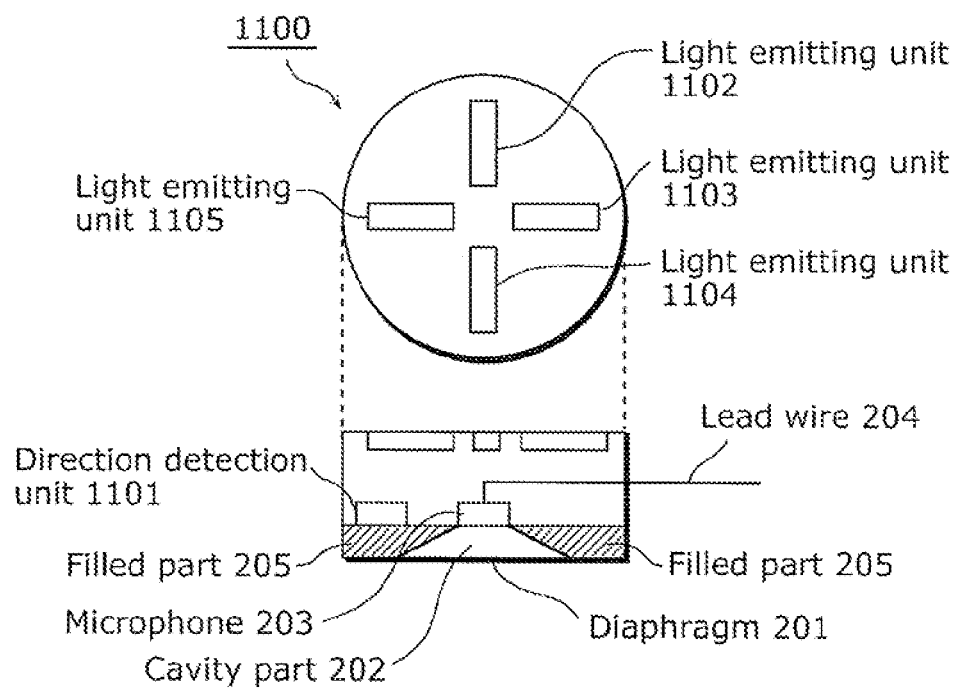
FIG. 14 is a diagram showing a schematic configuration of a physiological sound measurement unit in Embodiment 3.

FIG. 14 is a diagram showing a schematic configuration of a physiological sound measurement unit 1100 in Embodiment 3.

Note that the configuration of the physiological sound examination device 100 in Embodiment 3 except for the physiological sound measurement unit 1100 is basically the same as that of the physiological sound examination device 100 in Embodiment 1 or 2.

In the following, components identical to those in Embodiment 1 or 2 are assigned the same numerals used in Embodiment 1 or 2 and, therefore, the explanation of these components may be omitted.

The physiological sound measurement unit 1100 includes a direction detection unit 1101 which detects a predetermined direction, and light emitting units 1102, 1103, 1104, and 1105 each of which emits a warning light when the measurement position of the physiological sound is inappropriate.

Therefore, it can be said that, in the present embodiment, the display unit 107 having the light emitting units 1102 to 1105 is included in the physiological sound measurement unit 1100.

Figure 15:
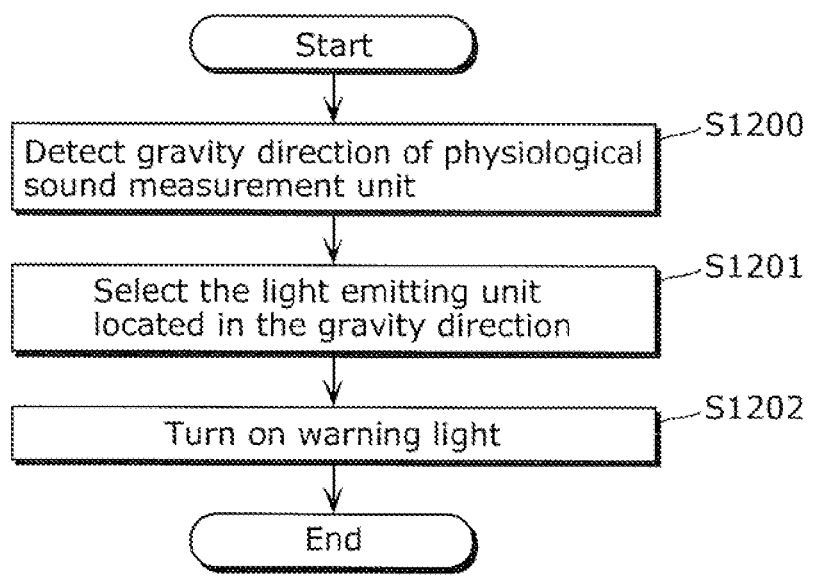
FIG. 15 is a flowchart showing an example of processing performed to turn on a warning light of the physiological sound measurement unit when a measurement position of the physiological sound is determined to be inappropriate.

The following describes an operation performed by the physiological sound examination device 100 when the measurement position of the physiological sound is determined to be inappropriate, with reference to FIG. 15.

FIG. 15 is a flowchart showing an example of processing performed to turn on a warning light of the physiological sound measurement unit 1100 when the measurement position of the physiological sound is determined to be inappropriate.

When the determination unit 2304 or 2403 determines that the measurement position of the physiological sound is inappropriate, the direction detection unit 1101 of the physiological sound measurement unit 1100 detects the predetermined direction. To be more specific, the direction of gravity is detected (S1200). It should be noted that a gyro sensor or an acceleration sensor is used as the direction detection unit 1101.

Next, the control unit 105 selects one of the light emitting units 1102 to 1105 that is located closest to the direction of gravity (S1201). Note that when two light emitting units are located closest to the direction of gravity, these two light emitting units may be selected.

Then, the light emitting unit selected in S1201 turns on the warning light (S1202).

More specifically, regardless of which direction the physiological sound measurement unit 1100 is placed on the measurement subject (that is, the circumferential direction in the upper portion of FIG. 14) when the physiological sound is measured, the light emitting unit closest to the direction of downforce at the time of measurement is selected and caused to emit light.

As described, the physiological sound examination device 100 in the present embodiment includes the light emitting units. To be more specific, the light emitting units 1102 to 1105 are arranged in the physiological sound measurement unit 1100. With this, the measurer can check to see whether or not the measurement position is appropriate without looking away from the physiological sound measurement unit 1100 or the measurement position.

For example, suppose that the measurer places the physiological sound measurement unit 1100 on the body at the position too close to the clavicle. In such a case, the measurement position is determined to be an inappropriate position which is too close to the clavicle, and the light emitting unit located in the direction of gravity, that is, the direction to which the physiological sound measurement unit 1100 is moved (the direction on the chest wall), turns on the warning light. This allows the measurer to easily find the appropriate measurement position.

It should be noted that, when the measurement position of the physiological sound is located on the rib, the light emitting unit located in the direction of the intercostal space emits light, so that the physiological sound measurement unit 1100 is moved to the intercostal space.

The physiological sound measurement unit 1100 may include only one light emitting unit. In this case, the direction detection unit 1101 is unnecessary. When the measurement position is determined to be inappropriate, this sole light emitting unit turns on the warning as light. This allows the measurer to check at least whether or not the measurement position is appropriate.

Moreover, since the number of parts included in the physiological sound measurement unit 1100 can be reduced in this case, the physiological sound measurement unit 1100 can be manufactured at low cost. Furthermore, this can also achieve the size and weight reduction of the physiological sound measurement unit 1100, thereby improving the measurement sensitivity of the physiological sound measurement unit 1100.

Note that the physiological sound measurement unit 1100 may include, instead of the light emitting unit, an audio output unit, such as a speaker, which sounds a warning beep when the measurement position is determined to be inappropriate. In this case, again, the physiological sound measurement unit 1100 can be manufactured at low cost and the size and weight reduction of the physiological sound measurement unit 1100 can be achieved.

In the present embodiment, the direction detection unit 1101 detects the direction of gravity. However, the predetermined direction detected by the direction detection unit 1101 is not limited to the direction of gravity. For example, the direction detection unit 1101 may detect a direction in which the clavicle is located or an opposite direction, that is, the upward direction on the body (the direction from the lower body to the upper body) or the downward direction on the body (the direction from the upper body to the lower body).

In this case, the filled part 205 or the diaphragm 201 may include a strain sensor which detects the downward direction based on that a strain is detected on the clavicle or rib. For example, the physiological sound measurement unit 1100 may include a plurality of strain sensors, and a direction opposite to the direction where the strain is detected may be detected as the downward direction. As a consequence, even when the measurement subject is in, for example, a supine position instead of an upright position while the physiological sound is being measured, the downward direction of the body can be detected.

Moreover, the direction detection unit 1101 may not be included in the physiological sound measurement unit 1100. For example, the direction detection unit 1101 may be implemented as a sensor provided outside the physiological sound measurement unit 1100.

Furthermore, the light emitting units 1102 to 1105 may not be arranged in the physiological sound measurement unit 1100, and may be included in, for example, the main unit of the physiological sound examination device 100 where the signal processing unit 104 and so forth are embedded. In this case, for example, each of the light emitting units 1102 to 1105 may receive the result of the direction detection performed by the direction detection unit 1101 included in the physiological sound measurement unit 1100, and then may emit light according to the result of the detection.

Embodiment 4

Figure 16:
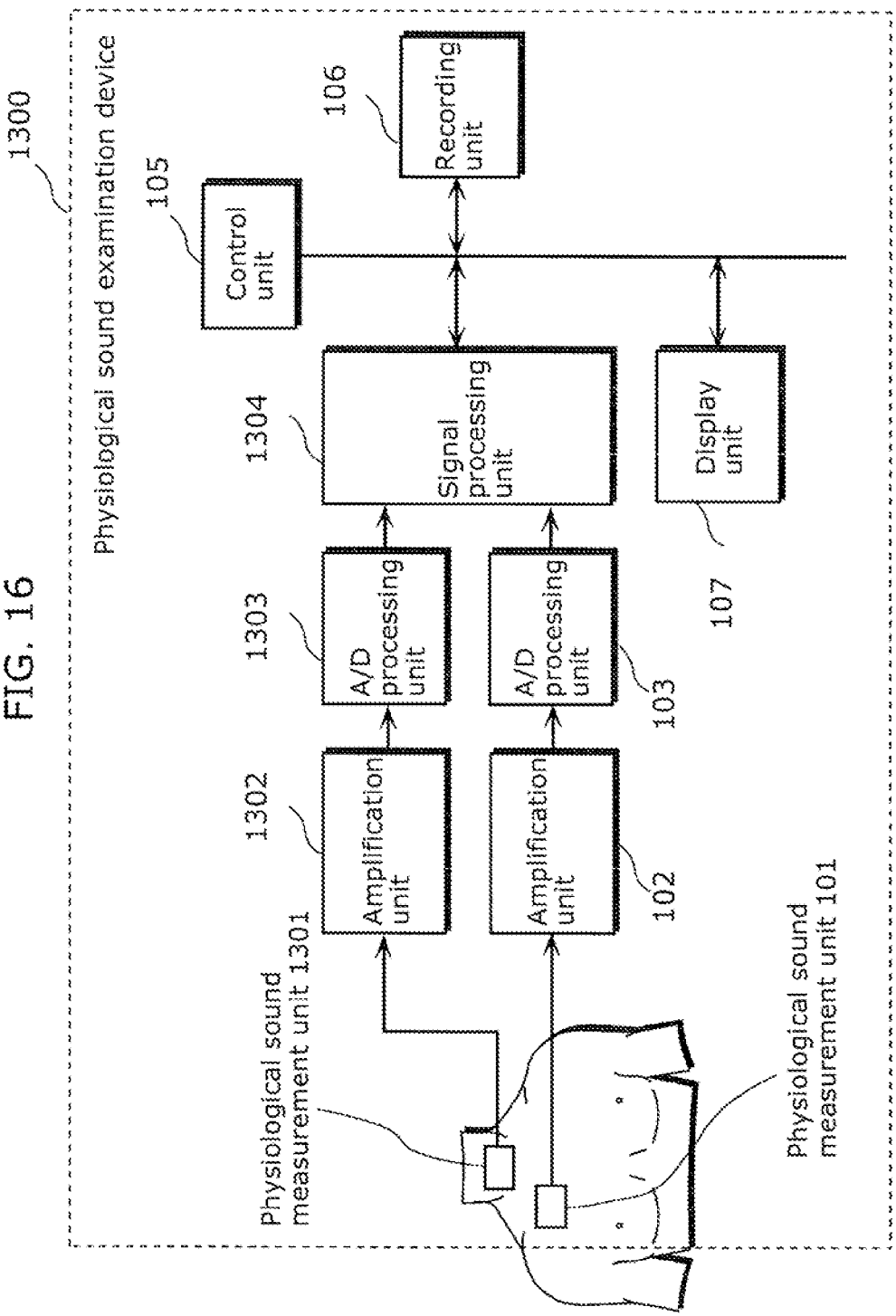
FIG. 16 is a diagram showing a basic configuration of a physiological sound examination device in Embodiment 4.
Figure 17:
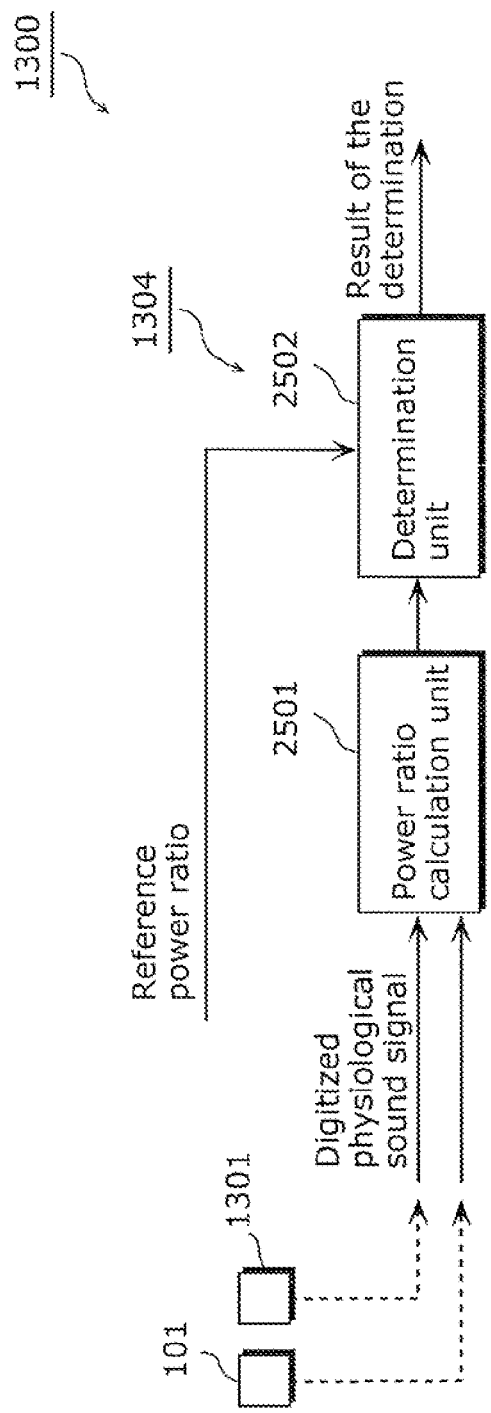
FIG. 17 is a diagram showing an example of a configuration of a signal processing unit in Embodiment 4.

FIG. 16 is a block diagram showing a basic configuration of a physiological sound examination device 1300 in Embodiment 4. FIG. 17 is a diagram showing an example of a configuration of a signal processing unit 1304 in Embodiment 4. In the following, components identical to those in Embodiment 1 are assigned the same numerals used in Embodiment 1 and, therefore, the explanation of these components may be omitted.

In addition to the configuration of the physiological sound examination device 100 in Embodiment 1, the physiological sound examination device 1300 further includes: a physiological sound measurement unit 1301 which measures a physiological sound; an amplification unit 1302 which amplifies a physiological sound signal measured by the physiological sound measurement unit 1301; and an A/D processing unit 1303 which converts the physiological sound signal having been amplified by the amplification unit 1302 into digital data. Moreover, the physiological sound examination device 1300 includes a signal processing unit 1304 instead of the signal processing unit 104.

The signal processing unit 1304 analyzes the physiological sound signals having been converted into the digital data by the A/D processing unit 103 and the A/D processing unit 1303.

The physiological sound measurement unit 1301 has the same configuration as the physiological sound measurement unit 101 (see FIG. 2). Moreover, as shown in FIG. 17, the signal processing unit 1304 calculates powers of two kinds of physiological sounds measured by the two physiological sound measurement units (i.e., 1301 and 101), and includes: a power ratio calculation unit 2502 which calculates a power ratio between the two kinds of physiological sounds; and a determination unit 2502 which compares the calculated power ratio with a reference power ratio to determine whether or not the measurement position is appropriate.

It should be noted that the power ratio calculation unit 2501 implements functions of a power calculation unit and a power comparison unit included in a physiological sound examination device according to an aspect of the present invention.

The two kinds of physiological sounds measured by the physiological sound measurement units 1301 and 101 are examples of the first physiological sound and the second physiological sound. Moreover, the powers of these two physiological sounds calculated by the power ratio calculation unit 2501 are examples of the first power and the second power.

Furthermore, the physiological sound measurement unit 1301 is an example of a first measurement unit, and the physiological sound measurement unit 101 is an example of a second measurement unit.

The physiological sound examination device 1300 in Embodiment 4 may include at least the physiological sound measurement unit 101, the physiological sound measurement unit 1301, the power ratio calculation unit 2501, and the determination unit 2502, as shown in FIG. 17.

Figure 18:
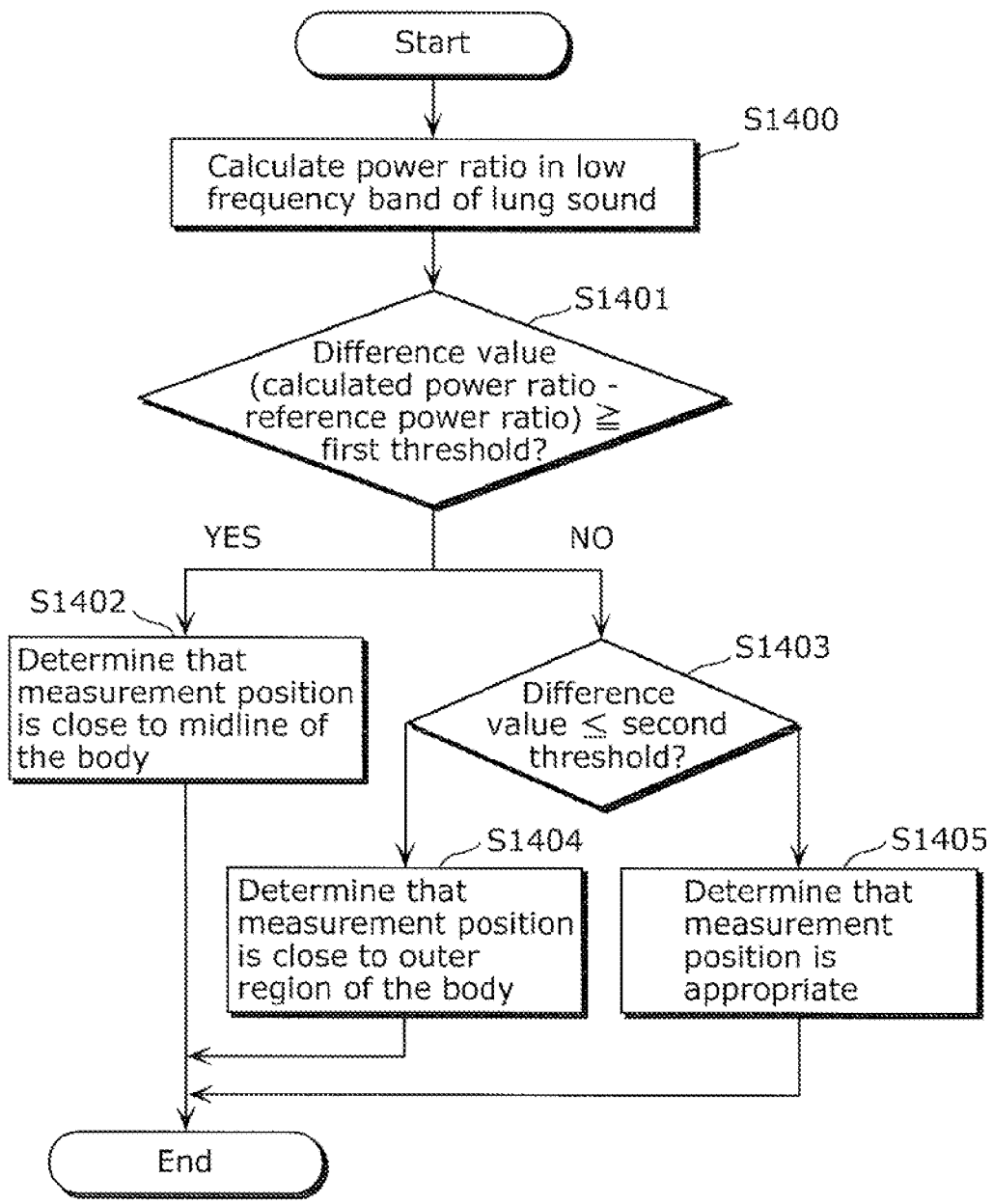
FIG. 18 is a flowchart showing an example of processing performed by the signal processing unit to determine whether or not a measurement position for the physiological sound measurement unit is appropriate on the chest wall.

The following describes an operation performed when the physiological sound examination device 1300 receives a physiological sound, with reference to FIG. 18.

FIG. 18 is a flowchart showing an example of processing performed by the signal processing unit 1304 to determine whether or not a measurement position for the physiological sound measurement unit 101 is appropriate on the chest wall.

When receiving the physiological sound signal from each of the A/D processing unit 103 and the A/D processing unit 1303, the power ratio calculation unit 2501 calculates a power ratio in the low frequency band of the lung sound between these physiological sound signals (S1400).

Here, as shown in FIG. 13, the spectral components of the lung sound are mostly included in the frequency band of not higher than 1 kHz. Thus, the frequency band for which the power ratio is calculated may be any frequency band which is not higher than 1 kHz.

However, as shown in FIG. 6, the spectral components of the heart sound are mostly included in the frequency band of not higher than 100 Hz. On this account, it is desirable that the low frequency band used for measuring the lung sound be particularly from 100 Hz to 200 Hz where it is unlikely to be influenced by the heart sound.

The power ratio is calculated as follows. Each of the powers of the two physiological sound signals in the frequency band from 100 Hz to 200 Hz is calculated, and then a ratio between these calculated powers is calculated. Each of the powers may be calculated by performing frequency conversion on the corresponding physiological sound signal and then calculating the power of the target frequency band from the power spectrum of the corresponding physiological sound signal. The power ratio may be calculated by a different method. More specifically, a spectrum may be calculated for each of the physiological sound signals via frequency conversion, and the power ratio may be calculated by a cross-spectral method.

Next, the determination unit 2502 calculates a difference between a reference power ratio and the power ratio calculated in S1400. Here, the reference power ratio is previously measured by the physiological sound examination device 1300 and stored in the recording unit 106. To be more specific, the determination unit 2502 determines whether a difference value obtained by subtracting the reference power ratio from the calculated power ratio is equal to or larger than a first threshold (S1401).

Here, the first threshold is determined by experiment, depending on: a measurement position determined according to a target physiological sound; the reproducibility of the sound; and the age and the like of the subject. For example, when the subject is an adult and the appropriate measurement position is located at the second intercostal space on the right midclavicular line, the first threshold may be "2 dB".

When determining, as a result of comparing the difference value and the first threshold, that the difference value is equal to or larger than the first threshold (Yes in S1401), the determination unit 2502 determines that the measurement position of the physiological sound measurement unit 101 is located closer to the midline of the body with respect to the appropriate position (S1402).

When determining that the difference value is smaller than the first threshold (No in S1401), the determination unit 2502 determines whether or not the difference value is equal to or smaller than a second threshold which is smaller than the first threshold (S1403).

Here, the second threshold is determined by experiment as well, depending on: a measurement position determined according to a target physiological sound; the reproducibility of the sound; and the age and the like of the subject. The second threshold may be a value obtained by reversing the sign of the first threshold. For example, when the subject is an adult and the appropriate measurement position is located at the second intercostal space on the right midclavicular line, the second threshold may be "−2 dB".

When determining, as a result of the comparison, that the difference value is equal to or smaller than the second threshold (Yes in S1403), the determination unit 2502 determines that the measurement position is located closer to the outer region of the body with respect to the appropriate position (S1404). When determining that the difference value is larger than the second threshold (No in S1403), the determination unit 2502 determines that the measurement position is appropriate (S1405).

Each of the processing steps is described in details as follows.

The reference power ratio used in S1401 refers to the power ratio in the low frequency band of the lung sound measured at the appropriate measurement position. Note that the method and frequency band used for calculating the reference power ratio are the same as those used in S1400.

The measurement position of the physiological sound measurement unit 101 refers to a desired position for listening to the physiological sound for the purposes, such as diagnosis. In order to measure, at high S/N, a sound source of the lung sound that is not an adventitious sound (namely, a breath sound), it is desirable for the measurement position of the physiological sound measurement unit 1301 to be at the sternal notch where a distance from the trachea to the body surface is short and where sounds of blood flows of the carotid artery and the jugular vein are unlikely to be heard.

Moreover, the denominator of the power ratio is the power related to the physiological sound measured at the sternal notch and the numerator is the power related to the physiological sound at the desired position.

The following are the reasons why the appropriateness of the measurement position can be determined from the power ratio in the low frequency band between the lung sounds measured at the different sites of the body.

The reasons are that: the power in the low frequency band of the lung sound propagating through the lungs during breathing is unlikely to be influenced by the presence or absence of a disease; and this power is attenuated depending significantly on a distance of propagation of the lung sound. It should be noted that the attenuation of the power in the low frequency band of the lung sound depending on this distance can be verified from a difference in the attenuation based on a difference between, for example, physical sizes.

Figure 19:
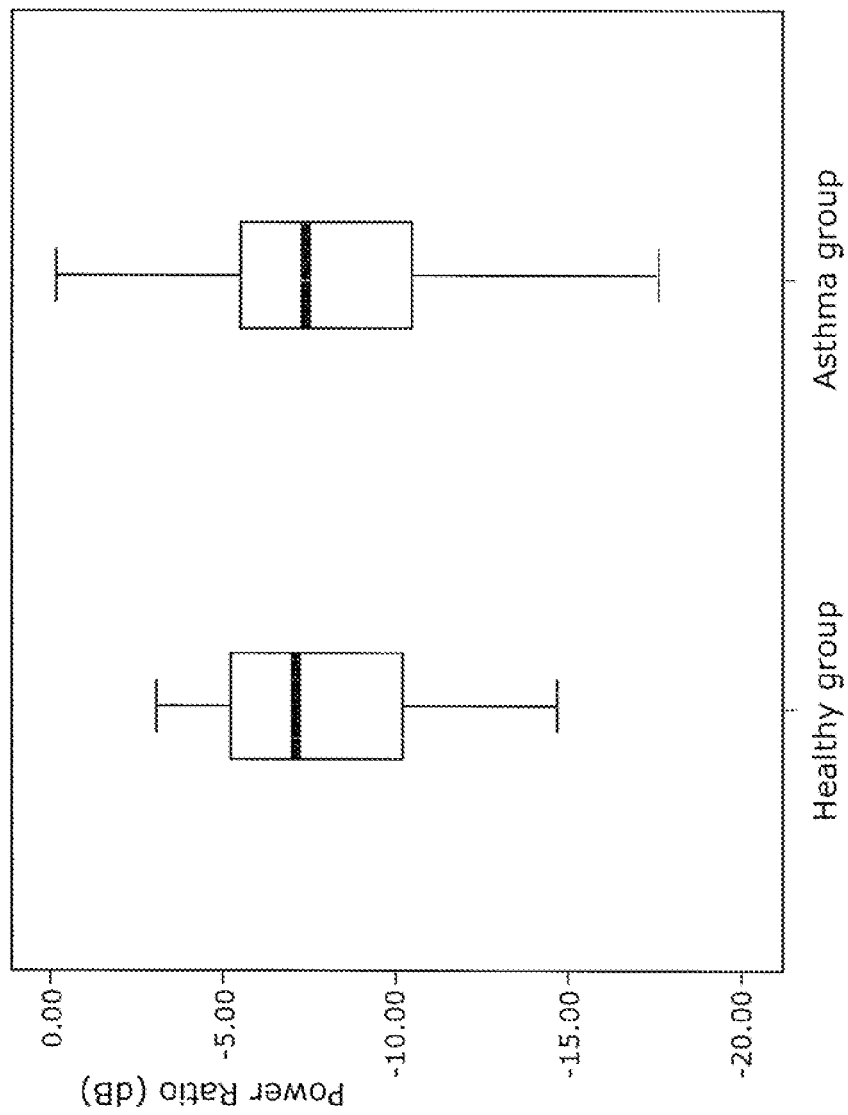
FIG. 19 is a diagram showing a result obtained by comparing power ratios in lung sound between a group of healthy people and a group of asthma patients.

FIG. 19 is a diagram showing a result obtained by comparing the power ratios in the frequency from 100 Hz to 200 Hz of the lung sound between a group of healthy people and a group of asthma patients (the number of the subjects is 262).

The measurement positions are located at the sternal notch and at the second intercostal space on the right midclavicular line. As shown in FIG. 19, no significant difference exists between average values indicated by thick lines corresponding to these groups. Thus, it can be said that the power ratio in the frequency band from 100 Hz to 200 Hz of the lung sound is not influenced by the presence or absence of asthma.

Figure 20:
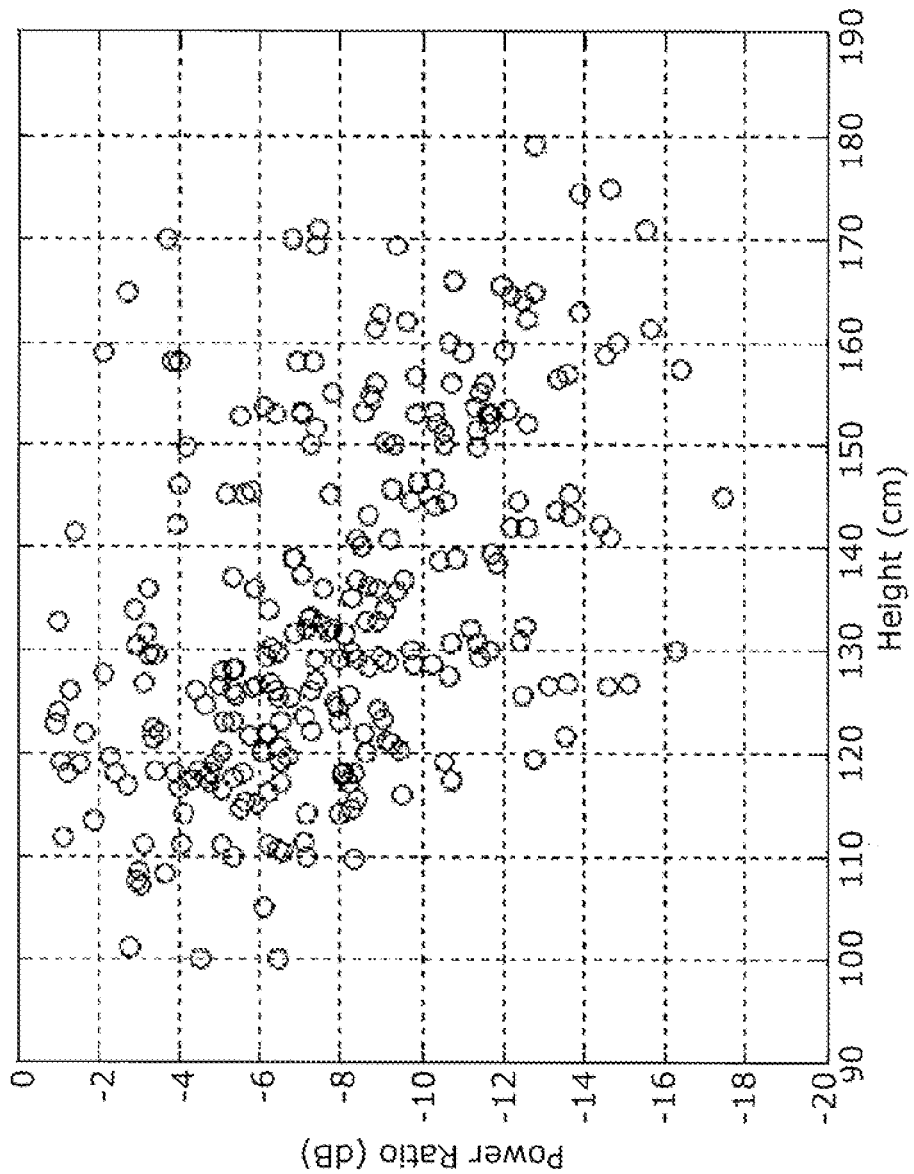
FIG. 20 is a diagram showing an example of a correlation between the height and the power ratio of the lung sound.

FIG. 20 is a diagram showing a correlation between the height and the power ratio in the frequency band from 100 Hz to 200 Hz of the lung sound (the number of the subject is 262). As shown in FIG. 20, a significant correlation exists between the height and the power ratio (correlation coefficient=−0.484, significance probability<0.001).

Here, the measurement positions are located at the sternal notch and at the second intercostal space on the right midclavicular line. Variations in the power ratio even in the case of the same height are results of a significant influence of differences among individuals, such as differences in the amount of fat or muscle. In general, when the height is increased, so do the lungs. That is why the distance of propagation of the lung sound is also increased.

Thus, in the case of one person, the power ratio in the low frequency band between the lung sounds measured at the two positions is unlikely to be influenced by a disease or a change in the amount of fat or muscle. Moreover, the power ratio significantly depends on the measurement position that is related to the distance of propagation of the lung sound.

Figures 21A, 21B:
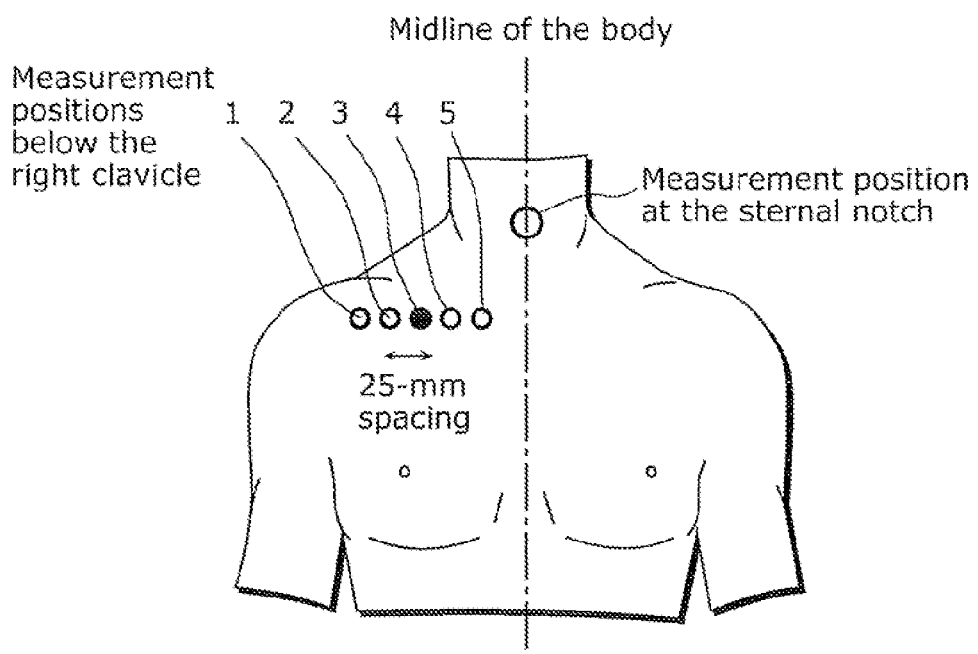
FIG. 21A is a diagram showing examples of different measurement positions below the right clavicle of one person.
FIG. 21B is a diagram showing a result obtained by measuring the power ratios of the lung sounds corresponding to the measurement positions shown in FIG. 21A.

FIG. 21A is a diagram showing examples of different measurement positions below the right clavicle of one person. FIG. 21B is a diagram showing a result obtained by measuring the power ratios in the frequency band from 100 Hz to 200 Hz of the lung sounds measured at the positions shown in FIG. 21A.

Note that Measurement position 3 is located at the second intercostal space on the right midclavicular line. The other measurement positions are located 25 mm and 50 mm away from Measurement position 3 to the side of the midline of the body and to the side of the outer region of the body.

As can be seen from FIG. 21B, as the measurement position is moved from the side of the midline of the body to the side of the outer region of the body, the power ratio in the frequency band from 100 Hz to 200 Hz of the lung sound decreases. Here, in the case of other than the adventitious sound, the lung sound refers to a sound heard as follows. That is, noise of turbulent air flow caused during breathing in the respiratory tract which is relatively large and vibration of the lining of the respiratory tract propagate through the lungs and are heard, as the lung sound, on the chest wall. The respiratory tract which is relatively large and is a sound source is located at the center side of the body. FIG. 21B indicates that the lung sound is significantly attenuated with distance from the midline of the body.

The processes performed in S1401 and the subsequent steps in FIG. 18 are described, with reference to FIG. 21A and FIG. 21B.

For example, suppose that the appropriate position where the reference power ratio is measured is Measurement position 3 (where the power ratio is −16.5 dB) and that the position where the measurement is performed for the re-examination is Measurement position 5 (where the power ratio is −10.7 dB). Moreover, suppose that the first threshold is 1.0 dB and that the second threshold is −1.0 dB.

Firstly, in S1401, the difference value is calculated at 5.8 dB=(−10.7)−(−16.5).

Next, in S1401, the difference value is determined to be equal to or larger than the first threshold. Then, in S1403, the measurement position is determined to be displaced toward the midline of the body with respect to the appropriate position.

Here, when the position for the re-examination is Measurement position 1 (where the power ratio is −24.5 dB), the difference value is calculated at −8.0 dB=(−24.5)−(−16.5) in S1401.

In S1401, the difference value is determined not to be equal to or larger than the first threshold. Then, in S1403, the difference value is determined to be equal to or smaller than the second threshold. Hence, in S1404, the measurement position is determined to be displaced toward the outer region of the body with respect to the appropriate position.

As described above, each of the first and second thresholds depends on a measurement position determined according to a target physiological sound and on the accuracy of the reproducibility. For example, suppose that the appropriate position is located at the second intercostal space on the right midclavicular line (i.e., Measurement position 3) and a margin of error for the measurement position is plus or minus 25 mm with respect to the appropriate position. In this case, it is effective to set the first threshold at +2 dB and the second threshold at −2 dB.

It should be obvious that the absolute values of the first and second thresholds may be different. For example, the first threshold may be +2 dB and the second threshold may be −2.5 dB.

When the measurement position is determined to be inappropriate in S1402 and in S1404, the control unit 105 may show the measurer that the measurement position is inappropriate or instruct the measurer to change the measurement position, using information display by the display unit 107.

Moreover, when the measurement position is determined to be closer to the midline of the body in S1403, the control unit 105 may cause the display unit 107 to display to the user that the measurement position is too close to the midline of the body and then may control the display unit 107 so that an instruction to move the measurement position outward on the body (to a position farther away from the midline of the body) may be indicated.

Similarly, when the measurement position is determined to be closer to the outer region of the body in S1405, the control unit 105 may cause the display unit 107 to display that the measurement position is too close to the outer region of the body (too far from the midline of the body) and then may cause the display unit 107 to give an instruction to move the measurement position inward on the body (to a position closer to the midline of the body) may be indicated.

Here, the question is: who measures the reference power ratio at the appropriate measurement position; and when this measurement is performed. For example, in the case of a patient who regularly goes to a hospital to see a doctor or has a checkup because of a chronic disorder or the like, a power ratio in the low frequency band of the lung sound measured for an examination at the appropriate measurement position by the doctor in the hospital or by an expert, such as a hospital laboratory technician, can be used as the reference power ratio.

Then, the reference power ratio measured in the hospital can be stored into the recording unit 106. With this, even when the patient is at home and the measurer is not an expert, the physiological sound can be measured, for the purpose of managing health care, at a measurement position similar to the position used by the expert.

The physiological sound examination device 1300 may include an input-output interface to an external recording medium, such as a memory card. With this configuration, the patient can record the result of the measurements made at home into, for example, the memory card and can bring the memory card to the hospital.

In this case, a reference power ratio measured for the examination in the hospital can be recorded into the memory card. Then, after the patient comes home, the memory card is connected to the physiological sound examination device 1300 in the home, so that the reference power ratio can be easily set and updated. It should be obvious that, instead of using the memory card, data may be sent and received between the hospital and the home via the Internet or the like.

As described thus far, by using the physiological sound examination device 1300, even a person who is not used to measuring the physiological sound can perform the measurement at a position close to the position used by the expert in the measurement. As a result, highly-reliable daily management data can be obtained. Thus, without being hospitalized, going to the hospital every day, or receiving home-visit care service, it is possible to manage the progression of the disease and the course of treatment at home. Alternatively, it may be possible to detect a disease at an early stage.

In the present embodiment, when the measurement position is determined to be inappropriate, the display unit 107 displays the warning to the measurer. However, control may be performed so that, based on the difference value used in S1401, the signal processing unit 1304 or the amplification unit 102 corrects the physiological sound signal measured by the physiological sound measurement unit 101.

For example, the frequency band of the lung sound in the physiological sound signal may be amplified by a level obtained by multiplying the difference value by −1. When the difference value is 3 dB, for instance, the frequency band of not higher than 1 kHz of the lung sound included in the physiological sound signal measured by the physiological sound unit 101 may be amplified by −3 dB.

More specifically, the amplification unit 102 may amplify the second physiological sound using a value obtained by reversing the sign of the difference value.

With this, even when the measurement position is not located at the correct position, the measurement position does not need to be changed. To be more specific, the physiological sound measured at an inappropriate position can be approximated to the signal power of the physiological sound measured at an appropriate position.

Moreover, even when the measurement position is not determined to be inappropriate, control may be performed so that, based on the difference value used in S1401, the signal processing unit 1304 or the amplification unit 1302 corrects the physiological sound signal measured by the physiological sound measurement unit 101.

With this, even when the measurement position is located at the correct position to some extent, the level of the power of the measured physiological sound signal can be approximated to the power of the physiological sound signal measured at the appropriate position. Accordingly, the accuracy of diagnosis by physiological sound analysis can be improved.

Embodiment 5

FIG. 22 is a flowchart showing an example of warning display processing performed when a measurement position of a physiological sound is determined to be inappropriate by a physiological sound examination device 1300 in Embodiment 5.

Note that the configuration of the physiological sound measurement unit 1100 in Embodiment 5 is the same as that of the physiological sound measurement unit 1100 in Embodiment 4.

Moreover, note that the configuration of the physiological sound examination device 1300 in Embodiment 5 is the same as that of the physiological sound examination device 1300 in Embodiment 4.

When the measurement position of the physiological sound is determined to be inappropriate by the physiological sound examination device 1300, the direction detection unit 1101 of the physiological sound measurement unit 1100 detects a predetermined direction in S1800. In the present embodiment, the direction of gravity is detected as the predetermined direction.

It should be noted that a gyro sensor or an acceleration sensor is used as the direction detection unit 1101 included in the physiological sound measurement unit 1100. Moreover, as in the case of Embodiment 3, the predetermined direction detected by the physiological sound measurement unit 1100 is not limited to the direction of gravity. For example, the direction in which the clavicle is located or the opposite direction, that is, the upward direction on the body or the downward direction on the body may be detected using a different sensor.

The following describes the processing in which the direction detection unit 1101 detects the direction of gravity as an example. Note that the same processing is performed in the case where the downward direction on the body is detected instead of the direction of gravity.

Next, the control unit 105 determines whether the result of determining the measurement position indicates that the measurement position is located closer to the midline of the body (S1801).

When the measurement position is determined to be closer to the midline of the body, the control unit 105 selects, from among the light emitting units, one or more light emitting units located on the left side (the left side as one faces the subject) of a gravity axis of the physiological sound measurement unit 1100 (S1802).

Note that the gravity axis refers to an axis passing through the physiological sound measurement unit 1100 and parallel to the direction of gravity. For example, the gravity axis passes through the center of the physiological sound measurement unit 1100 in a planar view (see the upper portion of FIG. 14) and is parallel to the direction of the gravity.

When the measurement position is not determined to be closer to the midline of the body, the control unit 105 selects, from among the light emitting units, one or more light emitting units located on the right side of the gravity axis (S1803).

Each of the light emitting units selected in S1802 and S1803 turns on a warning light by light emission (S1804).

Figure 23:
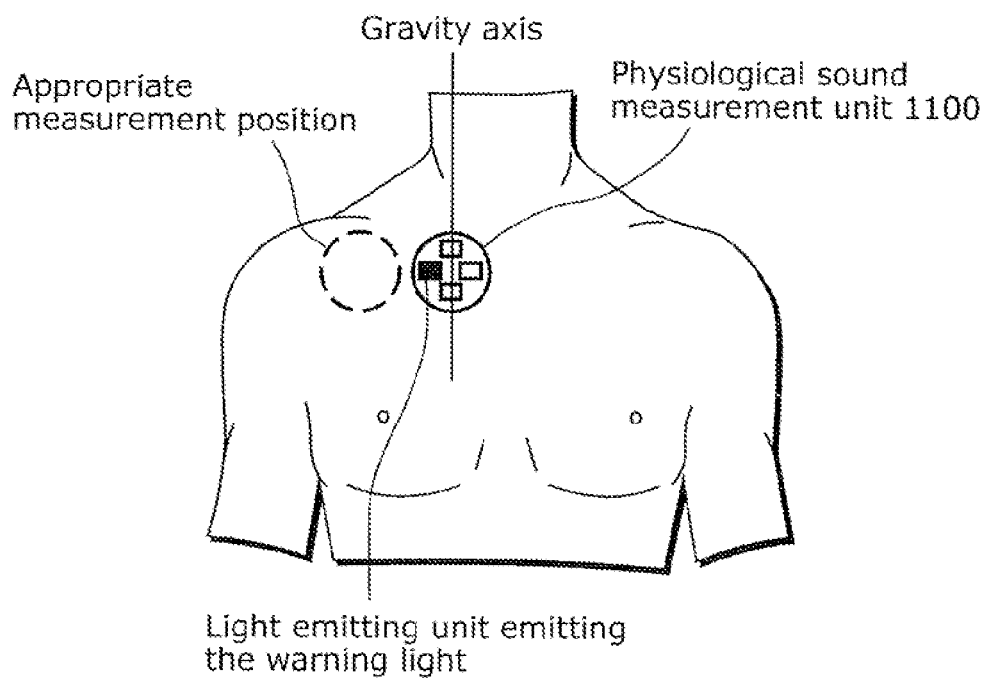

For example, suppose that the measurer places the physiological sound measurement unit on the body at a position closer to the midline of the body with respect to the appropriate measurement position, as shown in FIG. 23. In this case, the physiological sound examination device 1300 determines that the measurement position of the physiological sound is closer to the midline of the body and causes the light emitting unit located closer to the outer region of the body to turn on the warning light. With this, the measurer can be instructed to move the measurement position outward on the body.

In the above example, the appropriate measurement position is located on the right lung. When the appropriate measurement position is located on the left lung, the light emitting units selected in S1802 and S1803 are located in the directions opposite to the directions described above. Whether the appropriate position is located on the right lung or the left lung depends on a physiological sound of the measurement target, and may be determined in advance.

As described thus far, the measurer can check to see whether or not the measurement position is appropriate without looking away from the physiological sound measurement unit 1100 or the measurement position. This allows the measurer to easily find the appropriate measurement position.

The physiological sound measurement unit 1100 may include only one light emitting unit. In this case, the direction detection unit 1101 is unnecessary. When the measurement position is determined to be inappropriate, this sole light emitting unit turns on the warning light. This allows the measurer to check at least whether or not the measurement position is appropriate.

Moreover, since the number of parts included in the physiological sound measurement unit 1100 can be reduced in this case, the physiological sound measurement unit can be manufactured at low cost. Furthermore, this can also achieve the weight reduction of the physiological sound measurement unit 1100, thereby improving the measurement sensitivity of the physiological sound measurement unit 1100.

Furthermore, the physiological sound measurement unit 1100 in Embodiment 5 may also include an audio output unit, such as a speaker, as in the case of Embodiment 3.

Moreover, the direction detection unit 1101 and the light emitting units 1102 to 1105 in Embodiment 5 may be included in a unit or the like other than the physiological sound measurement unit 1100, as in the case of Embodiment 3.

Embodiment 6

Figure 24:
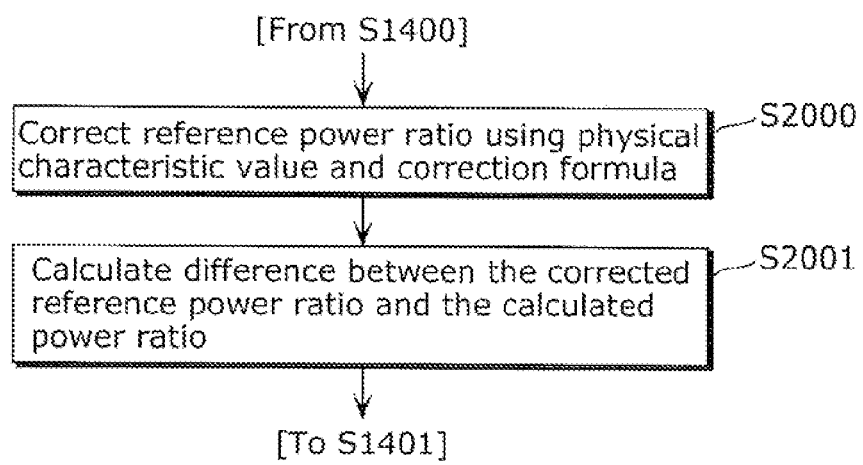
FIG. 24 is a diagram showing an example of a flow of processing performed by a physiological sound examination device in Embodiment 6.

FIG. 24 is a diagram showing an example of a flow of processing performed by a physiological sound examination device 1300 in Embodiment 6.

In the following, components identical to those in Embodiment 4 are assigned the same numerals used in Embodiment 4 and, therefore, the explanation of these components may be omitted.

The physiological sound examination device 1300 in Embodiment 6 performs the processing shown in FIG. 18, for example, as is the case with the physiological sound examination device 1300 in Embodiment 4. However, in S1401, a characteristic process is executed.

The following describes the flow of processing performed in S1401 in FIG. 18 by the physiological sound examination device 1300 in Embodiment 6 to calculate a difference between a reference power ratio and a power ratio of the measured lung sound, with reference to FIG. 24.

The determination unit 2502 corrects the reference power ratio using physical characteristic values and a correction formula (S2000). Here, the physical characteristic values indicate physical types of when the reference power ratio is set and of when the physiological sound is re-measured. The correction formula is previously stored in the recording unit 106. A correction method is described later in detail.

Moreover, in S2001, the determination unit 2502 calculates a difference between the corrected reference power ratio and the power ratio calculated in S1400 and performs comparison processing based on this difference value.

The correction method performed in S2000 is described as follows.

When age is used as the physical characteristic, the correction formula is expressed by Equation 1, for example.

$$\text{NewPow}R = \text{OrgPow}R - 0.583 * \delta Y \quad \text{Equation 1}$$

Here, "NewPowR" represents the corrected reference power ratio, "OrgPowR" represents the initial reference power ratio, and "$\delta Y$" represents the number of years elapsed from when the initial reference power ratio was set to when the re-measurement is performed. For example, when a half year has elapsed after the initial ratio was set, $\delta Y = 0.5$.

Suppose that the measurement subject is a ten-year-old child, that the initial reference power ratio is −8 dB, and that the re-measurement is performed after a half year after the initial set of the reference power ratio. In this case, the reference power ratio is corrected to −8.2915 dB (−8−0.583*0.5).

Note that, when age is used as the physical characteristic, the physiological sound examination device 1300 may include an interface unit using which a user can enter an age when the measurement is performed on the user for the first time. Then, the age may be stored, as the physical characteristic value, into the recording unit 106.

Moreover, every time the measurement is performed, age information may be updated via the interface unit. Alternatively, as in the above example, the recording unit 106 may store the measurement date in association with the age, so that an age of when a next measurement is performed may be determined based on a difference from a next measurement date.

Figure 25:
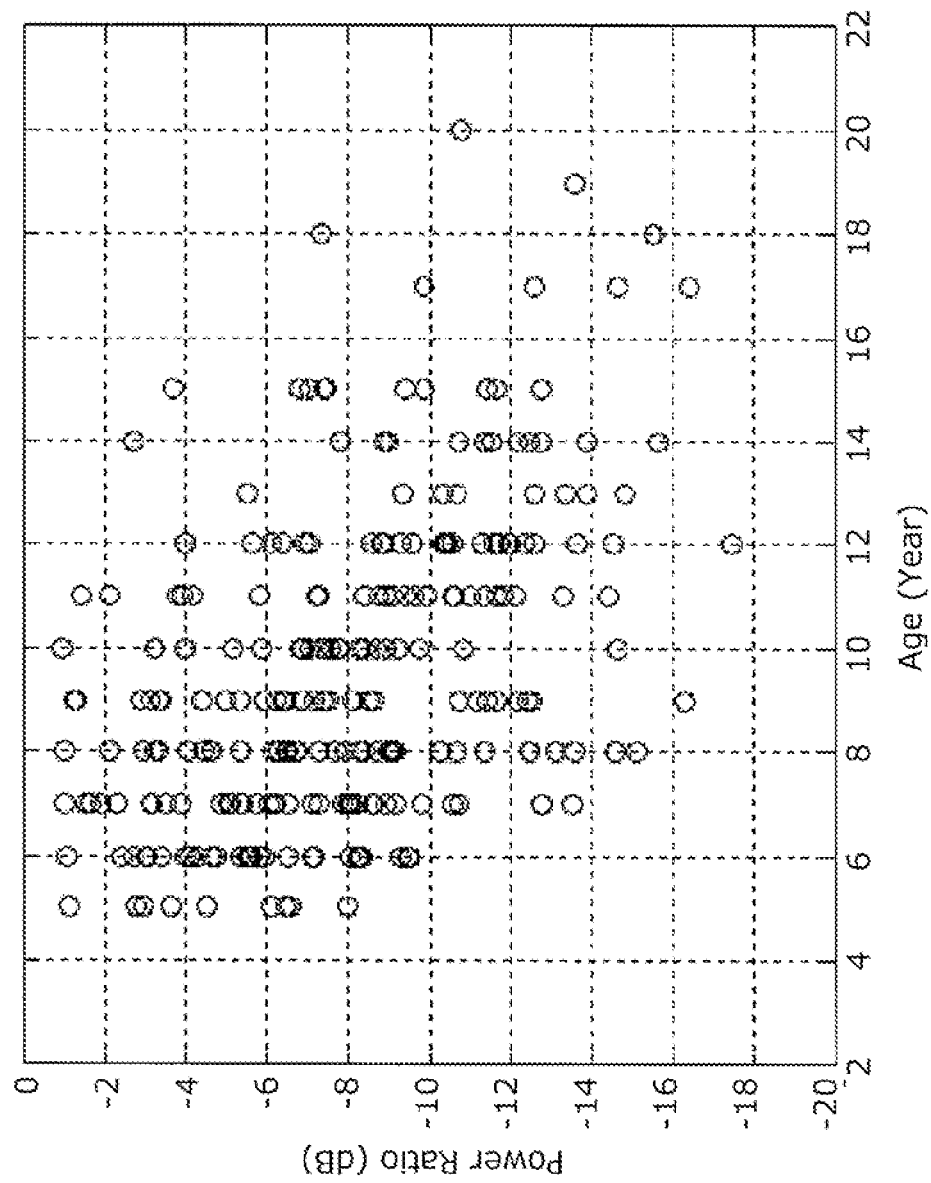
FIG. 25 is a diagram showing an example of a correlation between the age and the power ratio.

A coefficient of "−0.583" in Equation 1 is a slope of a regression line, as shown in FIG. 25, between the age and the power ratio in the frequency band from 100 Hz to 200 Hz of the lung sound.

A significant correlation exists between the age and the power ratio (correlation coefficient=−0.495, significance probability<0.001). The regression line in FIG. 25 can be expressed by Equation 2, for example.

$$\text{Pow}R = -0.583 * Y - 2.252 \qquad \text{Equation 2}$$

Here, "PowR" represents the power ratio in the frequency band from 100 Hz to 200 Hz of the lung sound, and "Y" represents the age.

The correction formula for the reference power ratio may be derived from a second- or higher-order regression curve. Suppose that the regression curve is expressed by PowR=f1(Y). In this case, the correction formula is expressed by Equation 3.

$$\text{NewPow}R = \text{OrgPow}R + (f1(Y2) - f1(Y1)) \qquad \text{Equation 3}$$

Here, "Y1" represents the age of when the reference power ratio was initially set, and "Y2" represents the age of when the re-measurement is performed.

Moreover, "f1(Y)" is an example of a prediction formula, and "f1(Y1)" and "f1(Y2)" are examples of a first predicted power ratio and a second predicted power ratio, respectively.

Changes in physical type in the course of growth slow down around adolescence. On this account, when the correction formula is derived from the slope of the regression line between the power ratio and the age, a target age may be specified. For example, the formula may be applied to a child aged 15 or younger.

Moreover, the correction of the reference power ration may be achieved by using the height as the physical characteristic value and a correction formula. FIG. 20 mentioned above is a diagram showing the correlation between the height and the power ratio in the frequency band from 100 Hz to 200 Hz of the lung sound. In this case, the regression line between the height and the power ratio is expressed by Equation 4, for example.

$$\text{Pow}R = -0.102 * H + 5.91 \qquad \text{Equation 4}$$

Here, "H" represents the height. When height is used as the physical characteristic, the physiological sound examination device 1300 may also include an interface unit using which a user can enter a height. Moreover, the interface unit may obtain the height of the user by connecting to, for example, a height measurement device. Alternatively, the measured height may be read from an external memory, such as an SD card, via the interface unit.

Thus, the correction formula for the reference power ratio using the height is expressed by Equation 5, for example.

$$\text{NewPow}R = \text{OrgPow}R - 0.102 * \delta H \qquad \text{Equation 5}$$

Here, "δH" represents a difference in the height between when the reference power ratio was initially set and when the re-measurement is performed. For example, suppose that the reference power ratio measured when a child was 120 cm in height is −5 dB and that the re-measurement is performed when the child is 130 cm in height. In this case, the reference power ratio is corrected to −6.02 dB (−5−0.102*10).

It should be noted that the correction formula for the reference power ratio may be derived from a second- or higher-order regression curve using the height. In this case, the correction formula is expressed by Equation 6.

$$\text{NewPow}R = \text{OrgPow}R + (f2(H2) - f2(H1)) \qquad \text{Equation 6}$$

A function "f2" is a regression curve of the power ratio in the frequency band from 100 Hz to 200 Hz of the lung sound and the height, and is an example of a prediction formula. Moreover, "H1" represents the height of when the reference power ratio was initially set, and "H2" represents the height of when the physiological sound is re-measured.

Moreover, "f2" is an example of a prediction formula, and "f2(H1)" and "f2(H2)" are examples of the first predicted power ratio and the second predicted power ratio, respectively.

Figure 26:
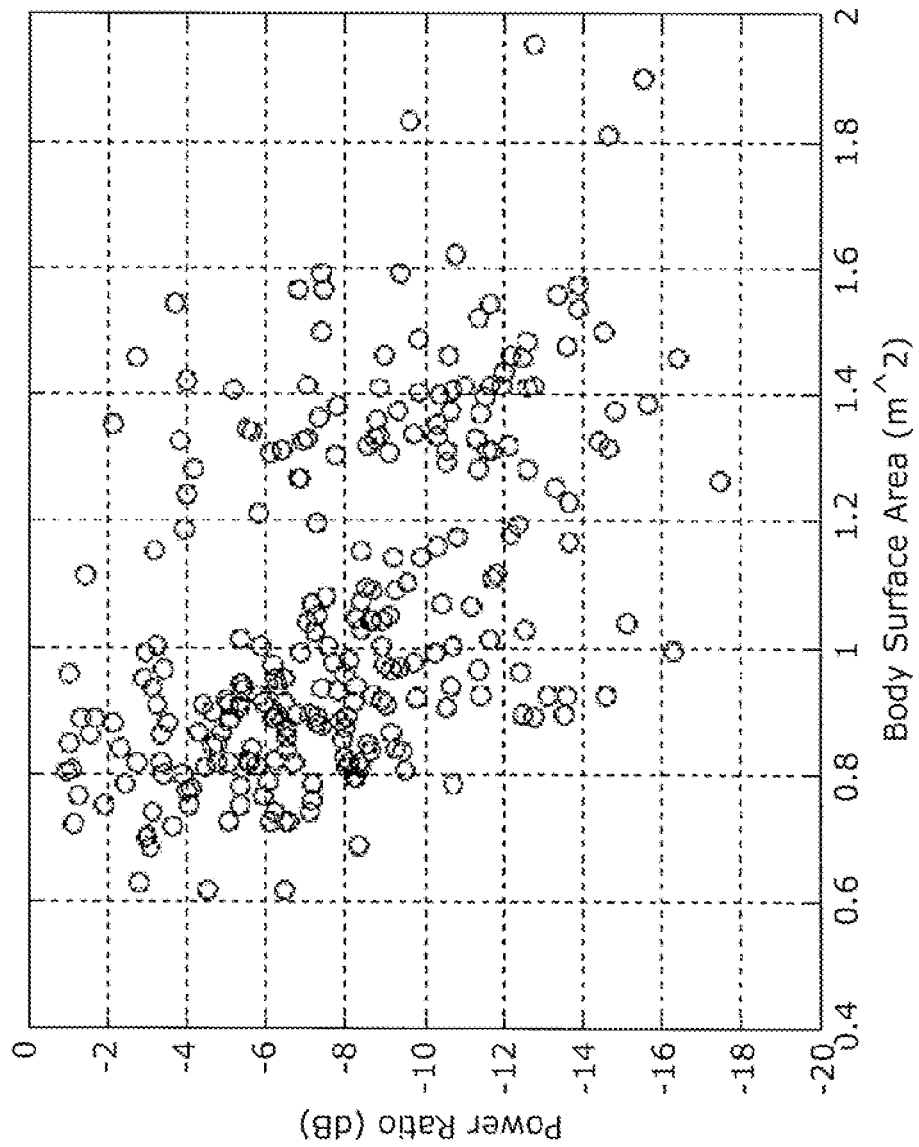
FIG. 26 is a diagram showing an example of a correlation between the body surface area and the power ratio of the lung sound.

Moreover, the correction of the reference power ration may be achieved by using a body surface area as the physical characteristic value and a correction formula. FIG. 26 is a diagram showing an example of a correlation between the body surface area and the power ratio in the frequency band from 100 Hz to 200 Hz of the lung sound.

Note that although a predictive value calculated from a height and weight according to Equation 7 is used as the body surface area, a different prediction formula may be used. The height and weight may be obtained from the interface unit as described above.

$$\text{BSA} = H^{(0.663)} * W^{(0.444)} * 0.008883 \qquad \text{Equation 7}$$

Here, "BSA" represents the body surface are (m^2), "H" represents the height (cm), and "W" represents the weight (kg). In FIG. 26, a significant correlation exists between the body surface area and the power ratio (correlation coefficient=−0.518, significance probability<0.001). In this case, the regression line can be expressed by Equation 8, for example.

$$\text{Pow}R = -6.947 * \text{BSA} - 0.416 \qquad \text{Equation 8}$$

Thus, the correction formula for the reference power ratio using the body surface area is expressed by Equation 9, for example.

$$\text{NewPow}R = \text{OrgPow}R - 6.947 * \delta \text{BSA} \qquad \text{Equation 9}$$

Here, "δBSA" represents a difference in the body surface area between when the reference power ratio was initially set and when the re-measurement is performed. For example, suppose that the reference power ratio measured when a child was 1.0 m^2 in body surface area is −9 dB and that the re-measurement is performed when the child is 1.1 m^2 in body surface area. In this case, the reference power ratio is corrected to −9.6947 dB (−9−6.947*0.1).

It should be noted that the correction formula for the reference power ratio may be derived from a second- or higher-order regression curve using the body surface area. In this case, the correction formula is expressed by Equation 10.

$$\text{NewPow}R = \text{OrgPow}R + (f3(\text{BSA2}) - f3(\text{BSA1})) \qquad \text{Equation 10}$$

A function "f3" is a regression curve of the power ratio in the frequency band from 100 Hz to 200 Hz of the lung sound and the body surface area. "BSA1" represents the body surface area of when the reference power ratio was initially set, and "BSA2" represents the body surface area of when the re-measurement is performed.

Moreover, "f3" is an example of a prediction formula, and "f3(BSA1)" and "f3(BSA2)" are examples of the first predicted power ratio and the second predicted power ratio, respectively.

Here, in the case where the correction is made based on the height or the body surface area, the correction can be made corresponding to the growth for each individual. Moreover, it is unnecessary to consider restriction of age or the like.

By the same method, the correction of the reference power ratio can be achieved using the weight or BMI. When the correction is made based on the age, the age may be set only once. Then, when the re-measurement is performed, the physiological sound examination device automatically calculates an elapsed time. Therefore, the height, weight, or the like does not need to be entered every time the measurement is performed, meaning that the measurer performs no burdensome operations. In addition, a mistake caused by an inputting error can be avoided.

Note that the physical characteristic value, such as the age, of when the reference power ratio was set is an example of a first physical characteristic value, and that the physical characteristic value, such as the age, of when the re-measurement is performed is an example of a second physical characteristic value. Moreover, each of $\delta Y$, $\delta H$, and $\delta BSA$ is an example of a value of the corresponding physical characteristic.

Suppose that a long time has elapsed after the reference power ratio was set, and that the distance of propagation of the lung sound changes due to the change in physical type. Even in such a case, the reference power ratio can be corrected using the physical characteristic value, as described thus far. As a consequence, even for a person who cannot go to a medical institution frequently and cannot update the reference power ratio for a long time, the physiological sound can be daily managed at home.

It should be noted that the regression lines or the correction formulas described above are only examples, and the present invention is not limited to these. For example, a formula including a different coefficient and constant may be employed. These values are coefficients calculated by a predetermined experiment. The power ratio decreases as the body size increases. On this account, a correction formula derived from the regression line can be employed almost in the same way as long as a slope coefficient is negative.

Moreover, the correction formula may include a plurality of physical characteristic values. In this case, the correction formula may be derived by multiple linear regression analysis performed on the physical characteristic values and the power ratio. Furthermore, the correction formula may vary according to the gender.

The above description assumes that the power ratio is expressed in decibels using a natural logarithm. When a natural logarithm is not used, amendments corresponding to the above description are required.

[Other Modifications]

Although the present invention has been described thus far based on Embodiments, the present invention is not limited to these Embodiments.

For example, the physiological sound measured, as the measurement target, by the physiological sound examination device 100 or 1300 may be a sound other than the heart sound and the lung sound. For example, the measurement target may be a sound of blood flowing in a predetermined part inside a living body.

In this case, the physiological sound examination device 100 or 1300 can determine, from two kinds of physiological sounds measured in different frequency bands or measured at different measurement positions, whether or not the measurement positions are appropriate for measuring the target blood flow sound.

The present invention further includes the following cases.

(1) Some or all of the components included in each of the above-described devices may be a computer system including a microprocessor, a ROM (Read Only Memory), a RAM (Random Access Memory), and a hard disk unit. The RAM or the hard disk unit stores a computer program implementing the same operation as performed by the corresponding above-described device. The microprocessor operates according to the computer program, so that function of the corresponding above-described device is carried out.

(2) Some or all of the components included in each of the above-described devices may be realized as a single system LSI (Large Scale Integration). The system LSI is a super multifunctional LSI manufactured by integrating a plurality of components onto a signal chip. To be more specific, the system LSI is a computer system including a microprocessor, a ROM, and a RAM. The RAM stores a computer program implementing the same operation as performed by the corresponding above-described device. The microprocessor operates according to the computer program, so that a function of the system LSI is carried out.

(3) Some or all of the components included in each of the above-described devices may be implemented as an IC card or a standalone module that can be inserted into and removed from the corresponding device. The IC card or the module is a computer system including a microprocessor, a ROM, and a RAM. The IC card or the module may include the aforementioned super multifunctional LSI. The microprocessor operates according to the computer program, so that a function of the IC card or the module is carried out. The IC card or the module may be tamper resistant.

(4) The present invention may be methods implemented by the computer processing described above. Each of the methods may be a computer program implemented by a computer, or may be a digital signal of the computer program.

Moreover, the present invention may be the aforementioned computer program or digital signal recorded on a computer-readable recording medium. As the computer-readable recording medium, a flexible disk, a hard disk, a CD-ROM, an MO, a DVD, a DVD-ROM, a DVD-RAM, a BD (Blu-ray Disc), or a semiconductor memory can be used. Also, the present invention may be the digital signal recorded on such a recording medium.

Furthermore, the present invention may be the aforementioned computer program or digital signal transmitted via a telecommunication line, a wireless or wired communication line, a network represented by the Internet, or data broadcasting.

Moreover, the present invention may be a computer system including a microprocessor and a memory. The memory may store the aforementioned computer program and the microprocessor may operate according to the computer program.

Furthermore, by transferring the recording medium having the aforementioned program or digital signal recorded thereon or by transferring the aforementioned program or digital signal via the aforementioned network or the like, the present invention may be implemented by a different independent computer system.

(5) Moreover, the above embodiments and modifications may be combined.

As described thus far, the physiological sound examination device according to the present invention has an advantageous effect by which even a person who is not used to measuring a physiological sound can measure the physiological sound at an accurate position. Thus, in a hospital or the like, a nurse may measure the physiological sound of an outpatient or an inpatient before a doctor sees the outpatient in outpatient setting or the inpatient while doing the rounds. Thus, the doctor does not need to perform auscultation when examining the patient, thereby reducing the length of examination time.

Even in the case where no doctor is with the patient because of remote medical care, a person who is not an expert can measure the physiological sound at the correct position. Thus, by transmitting the measured physiological sound to the doctor, the patient can receive a more detailed examination than an examination by interview.

Moreover, in the case of at-home management because of a chronic disorder or the like, a person who is not an expert can measure the physiological sound at an accurate auscultation position. Thus, the doctor can examine the highly-reliable daily physiological sound. This allows the doctor to easily manage the chronic disorder by, for example, checking the course of treatment and detecting the progression of the disease, which are difficult only in outpatient settings.

REFERENCE SIGNS LIST 100, 1300 Physiological sound examination device
101, 1100, 1301 Physiological sound measurement unit
102, 1302 Amplification unit
103, 1303 A/D processing unit
104, 1304 Signal processing unit
105 Control unit
106 Recording unit
107 Display unit
201 Diaphragm
202 Cavity part
203 Microphone
204 Lead wire
205 Filled part
1101 Direction detection unit
1102, 1103, 1104, 1105 Light emitting unit
2300 Power comparison unit
2301 Power calculation unit
2302 Extreme value detection unit
2303, 2402 Coincident period detection unit
2304, 2403, 2502 Determination unit
2401 Noise period detection unit
2501 Power ratio calculation unit

The invention claimed is:
1. A physiological sound examination device comprising:
a physiological sound measurement device configured to measure a physiological sound originating from vibration propagating through inside a living body of a measurement subject; and
a hardware processor,
wherein the hardware processor is configured to:
calculate power of a first physiological sound and power of a second physiological sound, the first physiological sound being one of two different kinds of physiological sounds measured by the physiological sound measurement device in a same time period and the second physiological sound being another of the two different kinds of physiological sounds,
compare first power indicating the power of the first physiological sound and second power indicating the power of the second physiological sound, to calculate a comparison result indicating a ratio or a difference between the first power and the second power, and
determine whether or not a measurement position of the physiological sound is appropriate, by comparing the comparison result with a threshold.
2. The physiological sound examination device according to claim 1, wherein the physiological sound measurement device includes:
a first measurement device configured to measure the physiological sound as the first physiological sound at a first site of the living body; and
a second measurement device configured to measure the physiological sound as the second physiological sound at a second site of the living body which is different from the first site, and
wherein the hardware processor is configured to calculate the comparison result indicating a power ratio in a predetermined frequency band between the first power and the second power, and determine that a measurement position of the second physiological sound is inappropriate when (a) a difference value obtained by subtracting a predetermined reference power ratio from the power ratio is equal to or larger than a first threshold used as the threshold or (b) the difference value is equal to or smaller than a second threshold smaller than the first threshold.
3. The physiological sound examination device according to claim 2,
wherein the first measurement device is configured to measure the physiological sound as the first physiological sound at a position, as the first site, where a sternal notch is located, and
the second measurement device is configured to measure the physiological sound as the second physiological sound at a position, as the second site, on a chest wall.
4. The physiological sound examination device according to claim 3, further comprising
a display unit configured to display an instruction, to the measurement subject or a measurer, to change the measurement position of the second physiological sound, when the hardware processor determines that the measurement position of the second physiological sound is inappropriate,
wherein the display unit is configured to
display the instruction to move the measurement position to a position farther away from a midline of the living body, when a result of the determination made by the hardware processor indicates that the difference value is equal to or larger than the first threshold, and
display the instruction to move the measurement position to a position closer to the midline of the living body, when the result of the determination indicates that the difference value is equal to or smaller than the second threshold.
5. The physiological sound examination device according to claim 4,
wherein the display unit includes at least one light emitting unit, and
the at least one light emitting unit is configured to display the instruction by emitting light, when the hardware processor determines that the measurement position of the second physiological sound is inappropriate.
6. The physiological sound examination device according to claim 5,
wherein the physiological sound measurement device further includes:
a direction detection sensor configured to detect, as a predetermined direction, a direction from an upper half of the living body to a lower half of the living body, when the hardware processor determines that the measurement position of the second physiological sound is inappropriate, and
wherein the display unit:
includes a plurality of light emitting units including the at least one light emitting unit;
is configured to cause a first light emitting unit, among the light emitting units, to emit light, when the result of the determination indicates that the difference value is equal to or larger than the first threshold, the first light emitting unit being located on a right side or a left side of an axis which passes through the second measurement device and is parallel to the detected predetermined direction; and is configured to cause a second light emitting unit, among the light emitting units, to emit light, when the result of the determination indicates that the difference value is equal to or smaller than the second threshold, the second light emitting unit being located on an opposite side of the axis with respect to the first light emitting unit.

7. The physiological sound examination device according to claim 6,
wherein the hardware processor is configured to perform a correction using: a first physical characteristic value indicating a physical characteristic value of the measurement subject of when the reference power ratio is set; a second physical characteristic value indicating a physical characteristic value of the measurement subject of when the first physiological sound and the second physiological sound are measured; and a preset correction formula.

8. The physiological sound examination device according to claim 7,
wherein, in the correction formula, a value obtained by multiplying a physical difference value between the first physical characteristic value and the second physical characteristic value by a predetermined coefficient is added to the reference power ratio which is to be corrected.

9. The physiological sound examination device according to claim 7,
wherein, in the correction formula, a correction difference value is added to the reference power ratio,
the correction difference value indicates a difference between a first predicted power ratio and a second predicted power ratio,
the first predicted power ratio indicates a value predicted from the first physical characteristic value, using a prediction formula for predicting the power ratio from the physical characteristic value, and
the second predicted power ratio indicates a value predicted from the second physical characteristic value, using the prediction formula.

10. The physiological sound examination device according to claim 7,
wherein each of the first physical characteristic value and the second physical characteristic value represents one of a height, an age, a weight, a body surface area, and a body mass index.

11. The physiological sound examination device according to claim 1, further comprising
an amplifier configured to amplify the second physiological sound using a value obtained by reversing a sign of the difference value.

12. The physiological sound examination device according to claim 1,
wherein the hardware processor is configured to (e) calculate, as the first power of the first physiological sound, power of the measured physiological sound in a first frequency band, and (f) calculate, as the second power of the second physiological sound, power of the measured physiological sound in a second frequency band different from the first frequency band,
(g) detect at least one pair of a first maximum value which is a maximum value in time-series data on the first power and a first time period including the first maximum value, and at least one pair of a second maximum value which is a maximum value in time-series data on the second power and a second time period including the second maximum value, (h) detect a coincident period which is coincident between the first time period and the second time period each of which is at least one in number, (i) calculate the comparison result indicating a difference between the first maximum value and the second maximum value included in the coincident period, the difference indicating the difference between the first power and the second power, and (j) determine that the measurement position of the physiological sound is inappropriate when the difference indicated by the comparison result is equal to or smaller than the threshold.

13. The physiological sound examination device according to claim 12,
wherein the hardware processor is configured to:
detect a low noise period which is included in a third frequency band of the physiological sound and in which power is equal to or smaller than a predetermined value, and
determine that the measurement position is appropriate when the coincident period is not detected from the low noise period.

14. The physiological sound examination device according to claim 12, further comprising
a display unit configured to display an instruction, to the measurement subject or a measurer, to change the measurement position, when the hardware processor determines that the measurement position is inappropriate.

15. The physiological sound examination device according to claim 14,
wherein the physiological sound is to be measured at a predetermined position near a predetermined bone, and
the display unit is configured to display the instruction to move the measurement position to a direction away from the predetermined bone, when the hardware processor determines that the measurement position is inappropriate.

16. The physiological sound examination device according to claim 14,
wherein the display unit includes at least one light emitting unit, and
the at least one light emitting unit is configured to display the instruction by emitting light, when the hardware processor determines that the measurement position is inappropriate.

17. The physiological sound examination device according to claim 16, further comprising
a direction detection unit configured to detect,
as a predetermined direction, a direction from an upper half of the living body to a lower half of the living body, when the hardware processor determines that the measurement position is inappropriate, and
the display unit:
includes a plurality of light emitting units including the at least one light emitting unit; and
is configured to cause one of the light emitting units to emit light, when the hardware processor determines that the measurement position is inappropriate, the one of the light emitting units being located closest to the predetermined direction.

18. The physiological sound examination device according to claim 12, wherein the first frequency band includes a frequency component lower than a frequency component included in the second frequency band.

19. The physiological sound examination device according to claim 13,
wherein the third frequency band includes a frequency component of a lung sound at 1 kHz or lower.

20. A physiological sound measurement method comprising:
measuring a physiological sound originating from vibration propagating through inside a living body of a measurement subject by a physiological sound measurement device;
calculating power of a first physiological sound and power of a second physiological sound, the first physiological sound being one of two different kinds of physiological sounds measured in the measuring step in a same time period and the second physiological sound being another of the two different kinds of physiological sounds by a hardware processor;
comparing first power indicating the power of the first physiological sound and second power indicating the power of the second physiological sound, to calculate a comparison result indicating a ratio or a difference between the first power and the second power by the hardware processor; and
determining whether or not a measurement position of the physiological sound measured in the measuring step is appropriate, by comparing the comparison result calculated in the comparing with a threshold by the hardware processor.

21. A non-transitory computer readable recording medium on which a program is recorded, the program causing a computer to execute:
calculating power of a first physiological sound and power of a second physiological sound, the first physiological sound being one of two different kinds of physiological sounds, which are originated from vibration propagating through inside a living body of a measurement subject, measured in a same time period and the second physiological sound being another of the two different kinds of physiological sounds;
comparing first power indicating the power of the first physiological sound and second power indicating the power of the second physiological sound, to calculate a comparison result indicating a ratio or a difference between the first power and the second power both calculated in the calculating; and
determining whether or not a measurement position of the physiological sound measured in the measuring is appropriate, by comparing the comparison result calculated in the comparing with a threshold.

22. An integrated circuit comprising:
a microprocessor; and
a non-transitory memory having stored thereon executable instructions, which when executed by the microprocessor, cause the integrated circuit to:
calculate power of a first physiological sound and power of a second physiological sound, the first physiological sound being one of two different kinds of physiological sounds measured in a same time period and the second physiological sound being another of the two different kinds of physiological sounds;
compare first power indicating the power of the first physiological sound and second power indicating the power of the second physiological sound;
calculate a comparison result indicating a ratio or a difference between the first power and the second power both calculated by the power calculation unit; and
determine whether or not a measurement position of the physiological sound is appropriate, by comparing the comparison result with a threshold.

* * * * *